(12) United States Patent
Cuevas Barragan et al.

(10) Patent No.: US 12,295,982 B2
(45) Date of Patent: May 13, 2025

(54) SYNERGISTIC COMPOSITION TO TREAT RESPIRATORY DISEASES AND STRENGTHEN THE IMMUNE SYSTEM TO FIGHT OTHER DISEASES AND PROCEDURE TO MANUFACTURE SUCH COMPOSITION

(71) Applicant: NasOil, S.A. de C.V., Jalisco (MX)

(72) Inventors: Carlos Eduardo Cuevas Barragan, Jalisco (MX); Elpidio Pena Beltran, Jalisco (MX)

(73) Assignee: NasOil, S.A. de C.V., Jalisco (MX)

( * ) Notice: Subject to any disclaimer, the term of this patent is extended or adjusted under 35 U.S.C. 154(b) by 531 days.

(21) Appl. No.: 17/477,997

(22) Filed: Sep. 17, 2021

(65) Prior Publication Data
US 2023/0103524 A1 Apr. 6, 2023

(51) Int. Cl.
| | | |
|---|---|---|
| *A61K 36/71* | (2006.01) | |
| *A61K 36/27* | (2006.01) | |
| *A61K 47/10* | (2017.01) | |
| *A61P 31/14* | (2006.01) | |
| *B01D 11/02* | (2006.01) | |
| *C11B 1/06* | (2006.01) | |

(52) U.S. Cl.
CPC .............. *A61K 36/71* (2013.01); *A61K 36/27* (2013.01); *A61K 47/10* (2013.01); *A61P 31/14* (2018.01); *B01D 11/0288* (2013.01); *B01D 11/0292* (2013.01); *C11B 1/06* (2013.01)

(58) Field of Classification Search
CPC ........ A61K 36/71; A61K 36/27; A61K 47/10; A61K 9/08; A61K 45/06; A61K 2236/00; A61P 31/14; B01D 11/0288; B01D 11/0292; C11B 1/06; A23D 9/007; A23L 33/115
See application file for complete search history.

(56) References Cited

U.S. PATENT DOCUMENTS

| | | |
|---|---|---|
| 4,986,985 A | 1/1991 | Grossman et al. |
| 5,178,865 A | 1/1993 | Ho et al. |
| 5,482,711 A | 1/1996 | Medenica |
| 2010/0292280 A1* | 11/2010 | Zachar .................. A61K 31/455 514/356 |
| 2020/0397711 A1 | 12/2020 | Lee |

OTHER PUBLICATIONS

Cuevas-Barragan CE, Buenrostro-Nava MT, Palos-Gömez GM, Ramirez-Padilla EA, Mendoza-Macias BI, Rivas-Caceres RR. Use of Nasoil® via intranasal to control the harmful effects of Covid-19. Microb Pathog. 2020;149:104504. doi: 10.1016/j.micpath.2020.104504.

Al-Ghamdi MS. The anti-inflammatory, analgesic and antipyretic activity of Nigella sativa. J Ethnopharmacol. 2001; 76:45-8.
Ankita S, Tribhuwan S, Rekha V. GC-Ms Analysis of bioactive phytoconstituents from *Rumex vesicarius* L. Int Res J Pharm 2015;6:269-72.
Dalle-Donne, I., Milzani, A., y Colombo, R. 2001a. Fluorometric detection of dityrosine coupled with HPLC separation for determining actin oxidation. Scientific Communications American Biotechnology Laboratory. 2001a; 34-36.
Dalle-Donne, I., Rossi, R., Giustarini, D., Gagliano, N. Lusini, L., Milzani, A., Di Simplicio, P. y Colombo, R. Actin carbonilation: from a simple marker of protein oxidation to revelant signs of several functional impairment. Free Radical Biology & Medicine. 2001b; 31: 1075-1083.
Denny, M. y Miller, L. Jet propulsion in the cold: mechanics of swimming in the Antarctic scallop Adamussium colbecki. The Journal of Experimental Biology. 2006; 209: 4503-4514.
El-Dakhakhny M, Mady NJ, Lembert N, Ammon HP. Nigella sativa oil, nigellone and derived thymoquinone inhibit synthesis of 5-lipoxygenase products in polymorphonuclear leukocytes from rats. J Ethnopharmaco. 2002; 81:161-4.
El-Dakhakhny M. Studies on the chemical constitution of the Egyptian *Nigella sativa* L. seeds. II: The essential oil. Planta Medica. 1963; 12:465-70.
El-Fatatry, H . . . "Isolation and structure assignment of an antimicrobial principle from the volatile oil of *Nigella sativa* L. seeds." Die Pharmazie 30 2 (1975): 109-11.
Enomoto S, Asano R, Iwahori Y, Narui T, Okada Y, Singab AN, Okuyama T. Hematological studies on black cumin oil from the seeds of *Nigella sativa* L. Biol Pharm Bull. 2001; 24:307-10.
Epstein, L. y Lapmort, D. T. A. An intramolecular linkage involving isodityrosine in extensine. Phytochemistry. 1984; 23: 1241-1246.
Evellyn CG, Priscila NC, Santos SG. Alpha-tocopherol and gamma-tocopherol concentration in vegetable oils. Food Sci Technol 2014; 34:379-85.
Fernández A. M. Usos de las especies del gënero *Asclepias* L. (Apocinaceae, Asclepiadoideae), información del herbario nacional de Mexico, Mexu. Polibotánica. 2008; 25: 151-171.
Fernández H. J. y Jordano B. D. La mariposa monarca *Dannus plexippus* (L., 1758) en el estrecho de Gibraltar (Lepidoptera:Danaidae). SHILAP Revista de Lepidopterología. 2009; 37 (148) 421-438.

(Continued)

*Primary Examiner* — Robert A Wax
*Assistant Examiner* — Quanglong N Truong
(74) *Attorney, Agent, or Firm* — Patenting Consulting Group; Roberto J. Rios

(57) ABSTRACT

A composition for treating respiratory diseases and strengthening the immune system is provided including a synergic mixture of a) oil extracted from seeds of the plant *Nigella sativa* diluted in propylene glycol with b) an alcoholic extract with ethanol obtained from aerial parts of the plant *Asclepias curassavica*. The composition is prepared by (a) extracting seed oil from the *Nigella sativa* plant, adding the extracted seed oil to propylene glycol; (b) macerating aerial parts of *Asclepias curassavica* plants in ethanol with a resting time if subjected to a water bath or another resting time without the water bath, straining and filtering; c) mixing a volume of the alcoholic extract of *Asclepias curassavica* with a volume of oil extracted from the seeds of the *Nigella sativa* plant diluted in propylene glycol; d) shaking and letting it rest.

26 Claims, 9 Drawing Sheets

(56) References Cited

OTHER PUBLICATIONS

Fry. S. C. Isodityrosine, a new cross-linking aminoacid from plant cell-wall glycoprotein. Biochemical Journal. 1982. 204: 449-455.

Gali-Muhtasib, Hala & El-Najjar, Nahed & Schhneider-stock, Regine. The medicinal potential of black seed (Nigella sativa) and its components. Advances in Phytomedicine. 2005; 2. 133-153. 10.1016/S1572-557X(05)02008-8.

Gerrard, J. A., Fayle, S. E., Brown, P. A., Sutton, L., Simmons, L. y Rasiah, I. Effects of microbial transglunaminase on the wheat proteins of bread and croissant dough. Journal of Food Science. 2001 ;66: 782-78.

Gilani A, Jabeen Q. and Khan M. A review of medicinal uses and pharmacological activities of Nigella sativa. Pakistan Journal of Biological Science. 2004; 7(4) 441-451.

Haas, F., Gorb S. y Blickhan, R. The function of resilin in beetle wings. Proceedings of the Royal Society B: Biological Sciences. 2000; 267: 1375-1381.

Hemadri R. S., Chakravarthi M., Chandrashekara K.N. and Naidu C. V. Phytochemical screening and antibacterial studies on Leaf and root extracto of *Asclepias curassavica* (L). Journal of Pharmacy and Biological Sciences. 2012; 2 (1) 39-44.

Jegadeeswari P, Nishanthini A, Muthukumarasamy S, Mohan VR. GC-MS analysis of bioactive components of Aristolochia krysagathra (Aristolochiaceae). J Curr Chem Pharm Sci 2012; 2:226-32.

Keeley, F. W., Bellingham, C. M. y Woodhouse, K. A. Elastin as a self-organizing biomaterial: use of recombinantly expressed human elastin polypeptides as a model for investigations of structure and self-assembly of elastin. Philosophical Transactions of the Royal Society B: Biological Sciences. 2002; 357: 185-189.

Knight, D. P. y Vollrath, F. Spinning an elastic ribbon of spider silk Philosophical Transactions of the Royal Society B: Biological Sciences. 2002; 357: 219-227.

Mahmound M.R., H.S. El-Abhar and S. Saleh. The effect of Nigella sativa oil against the liver damage induced by Schistosoma infection in mice. Journal of Ethnopharmacology. 2002. 79:1-11.

Murayama, K. Connectin/Titin, giant elastic protein of muscle. The Federation of American Societies for Experimental Biology Journal. 1997; 11: 341-345.

Pooja S, Ekta M, Rekha M. Identification of phytocomponents in the methanol extract of Cuscuta reflexa grown on Nerium oleander host plant through GC-MS analysis. Int J Pharm Bio Sci 2017;8:478-83.

Ricciardi-Verrastro B., Torres a. M., Camargo F. J. and Dellacassa E. S. Validación del uso tradicional de especies de Asclepias contra veneno de Bothrops diporus (yarará chica) en el Nordeste de Argentina. Boletin Latinoamericano y del Caribe de Plantas Medicinales y Aromáticas. 2016; 15(2): 112-121.

Rodríguez-Mateos, A., Millar, S. J., Bhandari, D. G. y Frazier, R. A. Formation of dityrosine cross-links during breadmaking. Journal of Agricultural and Food Chemistry 2006; 54: 2761-2766.

Sagert, J. y. Waite, J. H. Hyperunstable matrix proteins in the byssus of Mytilus galloprovincialis. The Journal of Experimental Biology. 2009; 212: 2224-2236.

Schrieber, R. and Gareis. 2007. Gelatin Handbook, Alemania, Wiley-VCH.

Shelke V. and Bhot M. GS-MS Analysis of bio-active compounds in ethanolic extracto of leaf and stem of *Asclepia curassavica* L. Int. J. Pharma. Investigation. 2019; 9 (2) 67-70.

Srivastava K.C. Extracts from two frequently consumed spices Cumin (*Cuminum cyminum*) and turmeric (*Curcuma longa*) inhibit platelet aggregation and alter eicosanoid biosynthesis in human blood platelets. Prostaglandins, leukotrienes, and essential fatty acids, 37(1), 57-64. https://doi.org/10.1016/0952-3278(89)90187-7.

Subbaiyan B, Jagatheskumar S, Mahendran G, Thangapandian V. Preliminary phytochemical screening, antibacterial activity and gas chromatography and mass spectrum analysis of Ceropegia bulbosa Roxb. (Aclepiadaceae). Int J Recent Adv Multidiscip Res 2015;2:841-7.

Sujayil, T.K. and Dhanaraj, T.S. Determination of Bioactive Compounds in Evolvulus alsinoides Leaf Extract using GC-MS Technique. Research Journal of Life Sciences, Bioinformatics, Pharmaceutical and Chemical Sciences.2016; 2,31-38.

Tatham, A. S. y Shewry, P. R. Comparative structures and properties of elastic proteins. Philosophical Transactions of the Royal Society B: Biological Sciences. 2002; 357: 229-234.

Tatham, A. S. y Shewry, P. R. Elastomeric proteins: biological roles, structures and mechanisms. Trends in Biochemical Sciences. 2000; 25: 567- 571.

Tilley, K. A., Benjamin, R. E., Bagorogoza, K. E., Okot-Kotber, B. M., Pakash, O. y Kwen, H. Tyrosine cross-links: molecular basis of gluten structure and function. Journal of Agricultural and Food Chemistry 2001; 49: 2627-2632.

Urry, D. W., Hugel, T., Seitz, M., Gaub, H. E, Sheiba, L., Dea, J., Xu, J. y Parker, T. Elastin: a representative ideal protein elastomer. Philosophical Transactions of the Royal Society B: Biological Sciences.2002; 357: 169-184.

Welch, K. D., Reilly, C. A. y Aust, S. D. The role of cysteine residues in the oxidation of ferritin. Free Radical Biology and Medicine. 2002; 33: 399-408.

* cited by examiner

SYNERGISTIC COMPOSITION TO TREAT RESPIRATORY DISEASES AND STRENGTHEN THE IMMUNE SYSTEM TO FIGHT OTHER DISEASES AND PROCEDURE TO MANUFACTURE SUCH COMPOSITION

FIELD OF INVENTION

Generally, this invention is aimed at the medicine and pharmacology fields, and particularly aimed at a synergistic composition of herbal essence to fight respiratory diseases and activate the immune system of the human body regarding fight infectious diseases caused by viruses and bacteria. In an even more specific level, this invention is aimed at the synergistic composition of the *Nigella sativa* Linn (*N. sativa*) vegetable seed extract and *Asclepias curassavica* aerial parts extracts (leaf, stalk, pod and flowers) and its use in treatments against symptoms of diseases related to changes in structural and functional proteins, such as those that constitute connective tissue, as some symptoms that can be alleviated by said extracts are related to respiratory, transmittable and allergic diseases.

BACKGROUND OF THE INVENTION

There are currently many herbal and plant extracts and preparations used to treat human diseases. Some preparations have been around for literally thousands of years, while others have been recently discovered. Effective plant extracts are highly demanded as a "natural" way of treating diseases. Natural preparations are believed to have a smaller toll on the human body than synthetic preparations.

Drug resistance is a global concern, as drug-resistant infections are increasing worldwide. According to the World Health Organization (WHO), nearly 700.000 people from around the world die every year due to drug-resistant infections. This and other factors have led WHO to anticipate a dramatic increase in the seriousness of drug-resistant infections. Deaths related to drug-resistant infections are expected to increase up to 10 million worldwide in 2050.

The excessive and widespread consumption of antibiotics by human beings, as well as the use of such antibiotics in livestock to improve both the characteristics and performance of production, and not necessarily to fight possible infections, are important factors of mutations in new drug-resistant superbugs. New infections transmissible by drug-resistant vectors are likely to come from such animals.

Such superbugs are able to spread across the environment through different vectors that feed on superbug-infected animals and further transmit the disease to humans, pets and other animals. These superbugs can also be spread by contaminated drinking water or irrigation water.

The enhancement of drug resistance and therefore the creation of super-microorganisms is rooted in the lack of an appropriate surveillance of the use of antibiotics in livestock. Therefore, we need alternatives aimed at avoiding drug resistance or the creation of microorganisms; one of these alternatives is the use of vegetable extracts.

In the 2008 World Health Organization (WHO) annual report, primary care is considered as the backbone of a proper health system. As part of the recommendations issued after 30 years of studies, WHO insists on the comprehensiveness and multifunctionality of primary care. Acute and chronic respiratory diseases are the main cause of consultations in primary care, as they also lead to disabilities and even death. Chronic diseases have increased due to populational ageing, cumulative exposition to tobacco use, air pollution, working environment, or contamination by biomass in rural or urban properties. Likewise, such diseases are both subdiagnosed and subtreated. Some other known factors are the overconsumption of antibiotics for viral respiratory infections, the consumption of non-effective respiratory symptoms, the lack of smear microscopies requested on chronic coughs, the underuse of inhaled steroids by asthmatics, poor COPD spirometry tests, the lack of anti-tobacco advises and underconsumption of anti-tobacco medications (Pérez-Padilla R., "Hacia un programa de prevención y atención primaria de enfermedades respiratorias, AIREa (Acción Integrada por la Respiración)". Neumol Cir Torax. 2012; 71 (3): 244-249).

Coronavirus have also been extracted from different animals and birds, causing a large variety of respiratory, gastrointestinal, neurological and systemic diseases in several species that have been later identified in humans. Since the mid-1960s, human coronaviruses have been identified as CoVH-229E (cluster 1) y CoVH-OC43 (cluster 2); such diseases have been linked to common cold and were considered to be relatively non-malignant respiratory pathogens. This notion changed in 2003, when a new coronavirus was found in China to be the cause of severe acute respiratory syndrome coronavirus in humans (CoVH-SARS), which caused atypical pneumonia with a ~10% mortality rate. It showed a high contagiousness in health centers and among the general population, as it reached almost 30 countries and disappeared after a few months. The high morbidity and mortality related to the outbreak of Severe Acute Respiratory Syndrome (SARS) has reactivated the interest to study this type of diseases and enabled the identification of new coronaviruses related to respiratory diseases: coronavirus NL63 (CoVH-NL63), coronavirus HKUI and Middle East respiratory syndrome-related coronavirus (MERS). Since its discovery, respiratory infection cases have been related to it, which suggests a universal distribution thereof. According to publications, the first two are relatively detected in patients coinfected with other respiratory viruses, as winter and spring register maximum levels amid poliannual waves. Coronavirus-related Middle East severe acute respiratory syndrome (CoVH-MERS) was first discovered in Saudi Arabia in 2012; camels are its natural host, while humans can be infected via interhuman transmission (Serra Valdés MA. "Infección respiratoria aguda por COVID-19: una amenaza evidente.", Rev Haban Cienc Méd, 2020, 19 (1): 1-5).

Coronaviruses are part of the family Coronaviridae, which consists of two subfamilies: Coronavirinae and Torovirinae. These are single-stranded RNA viruses. Nowadays, coronaviruses are divided in four genres: $\alpha$, $\beta$, $\gamma$, $\delta$. 229E and NL63 are $\alpha$-coronaviruses, while OC43 and HKUI or $\beta$-coronavirus. SARS and MERS are $\beta$-coronavirus of different descent. The detection and classification of new coronaviruses found in bats and other animals has widened our knowledge on coronavirus diversity, which is likely to keep increasing.

An international warning has circulated since the beginning of January across the entire media, social networks and WHO and PAHO announcements: the emergence of a new coronavirus known as 2019 nCoV, which is highly contagious between humans and causes a febrile respiratory illness with general symptoms, rhinorrhea, severe coughing and dyspnea, and the possibility of vomiting and diarrhea. According to preliminary reports, approximately 10-25% of cases suffer from severe acute respiratory syndrome or severe pneumonia that could lead to a highly mortal multisystem organ failure. Thorax radiography shows a bilateral interstitial infiltrate. Older patients and patients with comorbidities present the most severe cases (Serra Valdés MA. "Infección respiratoria aguda por COVID-19: una amenaza evidente.", Rev Haban Cienc Méd, 2020, 19 (1): 1-5).

According to WHO, COVID-19 is a diseased caused by the novel coronavirus known as SARS-COV-2. WHO first learned about the existence of this new virus on Dec. 31, 2019, as a cluster of patients infected with «viral pneumonia» was reported in Wuhan.

Most symptomatic patients (around 80%) recover without requiring medical treatment in a hospital. Around 15% suffer from severe illness and require oxygen therapy, and 5% will present critical conditions that require intensive care.

Some fatal difficulties are respiratory insufficiency, acute respiratory distress syndrome, sepsis and septic shock, thromboembolism and/or multiple organ dysfunction, including cardiac, hepatic and kidney injuries.

Furthermore, there are reports of severe damages in patients who overcame COVID-19; however, persistent damages in organs such as lungs, kidneys, heart have been reported. Thus, some patients who overcame the infection are left with a weaker, unresponsive immune system, which increases the risk of opportunistic infections and diseases.

There were no antiviral treatments, medications or vaccines that could control or reduce symptoms or keep the illness from worsening at the beginning of the pandemic. Some substances were tested as the pandemic went on, such as hydroxychloroquine, antiviral combinations—lopinavir/ritonavir—and interferon, which appeared to have little or no positive impact on the 28-day mortality or on hospitalized patients. Other antivirals such as remdesivir were also tested; however, even as expectations were encouraging, the cost was too high. Some anti-parasitic substances were also tested, such as ivermectin which could prevent Sars-COV-2 from replicating in in-vitro studies, as the Antiviral Research journal published. Many other substances were also tested in a number of studies. According to WHO, a vaccine is a preparation that is used to provide immunity against a disease by stimulating the production of antibodies.

The use of vaccines in the control of infectious diseases has been largely successful in altering incidence and mortality patterns of smallpox, polio, measles, rubella, tuberculosis, pertussis, diphtheria, etc., and have had a larger impact on the public health than healing treatments based on antimicrobials against infectious diseases (GARCIA, Fernando, "Métodos moleculares para el desarrollo de vacunas.", Acta pediátr. costarric, 1999, vol. 13, n. 2, pp. 55-59).

There are currently a number of vaccines against Sars-COV-2. There are different vaccine brands, but there are three main methods of vaccine manufacturing according to WHO: a) use a whole virus or bacteria, b) use pieces that induce a response by the immune system and c) use the genetic material alone.

The method in which the whole pathogen agent is used is i) inactivated vaccines in which the pathogenic virus or bacteria, or a similar specimen, is isolated and then inactivated or destroyed by chemical substances, heat or radiation; however, the conduction of such method requires special laboratories to safely grow the virus or bacteria; this technique usually requires relatively long manufacturing periods, and the resulting vaccines are commonly administered as two-or three-doses series. II) Attenuated vaccines use a pathogenic virus or a similar specimen and maintain it activated but weakened. Such strategy uses technology similar to that of inactivated vaccines; furthermore, it allows for a large vaccine manufacturing. However, in many cases the administration of this type of vaccines is not advised for immunocompromised patient. III) Vaccines based on viral vectors use an innocuous virus to transport specific pieces (called "proteins") of the relevant pathogenic agent in order to have them provoke an immune response without actually causing illness. To achieve such purpose, instructions to manufacture specific pieces of the relevant pathogenic agent are administered into an innocuous virus. Subsequently, the innocuous virus works as a platform (a «vector») to introduce the protein into the organism. Afterwards, the protein produces an immune response.

The vaccine manufacturing methods that use an antigenic subunit are those that only work with specific pieces (called "antigenic subunits") of the virus or bacteria that the immune system must assimilate. These vaccines do not contain the whole pathogenic agent, nor use an innocuous virus as vector. Antigenic subunits are usually proteins or carbohydrates.

The genetic method (nucleic acid vaccines) only uses a genetic material sequence that provides instructions to manufacture specific proteins and not the whole agent. DNA and RNA molecules are the instructions our cells follow to produce proteins. Firstly, the DNA code in our cells transduces into a messenger RNA that is subsequently used as a template to produce specific proteins. Nucleic acid vaccines insert a specific set of instructions into our cells, whether as DNA or mRNA, in order to produce the specific protein, the immune system is expected to assimilate and against which a response is induced. Because of the pandemic, research on this field has progressed rapidly and an emergency use authorization has been granted to some mRNA vaccines against COVID-19, which means that people can now be vaccinated outside clinical trials.

Vaccine development requires in any case a considerable amount of time and requires procedures and methods extremely expensive, and precisely the need to vaccinate people in the short term has accelerated the processes to enable its emergency use authorization. However, not all countries have the same access to vaccines, due to disparity in availability or the high cost some countries must endure to vaccine their population.

Some of the most renowned vaccines that have received an emergency use authorization are AZD1222 by AstraZeneca and the University of Oxford Ltd., which is a recombinant vaccine such as the Janssen JNJ-78436735 vaccine by Johnson & Johnson, which uses a recombinant adenoviral vector that includes the sequence that codes the spike protein(S) of the SARS-COV-2 virus, the mRNA-1273 vaccine by Moderna (with modified nucleosides), the COVID-19 BIBP vaccine by Sinopharm, also known as COVID-19 inactivated vaccine (VERO CELL) is manufactured in Vero cells and becomes inactivated by β-Propiolactone, the CoronaVac vaccine by Sinovac Biotech, which is also an inactivated vaccine that uses SARS-COV-2 (the virus that causes COVID-19) particles obtained from cultures, the mRNA-type BNT162b2 vaccine by Pfizer, Inc. and BioNTech; the CanSino vaccine by CanSino Biologics Inc. based on a non-replicating viral vector; and the Sputnik V vaccine by the Gamaleya Research Institute, based on a non-replicating viral vector.

Nevertheless, and despite many vaccines are now available, its high demand has prevented them from reaching a lot of countries and large numbers of inhabitants and therefore contribute to reducing COVID-19 contagions. Thus, new compositions, natural formulations or products, or new drugs that help us mitigate the pandemic on a global scale are still needed.

This invention is aimed at a synergistic composition based on the extracts of two plants used to treat different respiratory diseases, such as COVID-19, strengthen the immune system to fight other diseases and a method to produce such composition.

According to Sally Robertson, January 2021, American researchers have found that the extracts of an aromatic herb called *Artemisia annua* prevent the severe acute respiratory syndrome coronavirus (SARS-COV-2)—the agent that causes the current pandemic disease COVID-19—from replicating. Also known as "sweet wormwood", ragweed is an Asian herb that produces artemisinin, an agent to treat malaria. Currently, researchers from the University of Columbia in the City of New York, the University of Washington and the Worcester Polytechnic Institute have found that leaf extracts from Wormwood based on artemisinin in hot water have antiviral components useful against SARS-COV-2.

The plant *Nigella sativa* has a wide range of medical applications. It is an annual herb, part of the Rannunculaceae family. Other *Nigella* species are *Nigella arvensis* and *Nigella damascena*. *Nigella sativa* features an erect and ramified stem, and feathery, grayish green, alternate leaves. Star-shaped bluish white leaves are terminal. Petals are not there. Fruit is a spherical capsule with small, dark, rough seeds on it. The plant comes mainly from India, Bangladesh, Turkey, the Middle East and the Mediterranean basin. Its seeds are known as "black cumin", used mostly for alimentary and medical purposes, such as spices and in the treatment of different diseases.

*Nigella sativa* has been reported to be used in Egyptian medicine as both a diuretic and carminative. The oil is used to treat asthma, respiratory distress and cough. The active principle, called nigella, has been isolated from the volatile oil fraction and has been reported to be useful in the treatment of bronchial asthma (Gilani A, Jabeen Q. and Khan M. "A review of medicinal uses and pharmacological activities of *Nigella sativa*.", Pakistan Journal of Biological Science. 2004; 7 (4) 441-451).

The extract from seeds in 1000-62.58 ppm concentrations in petroleum ether has reportedly the same capacities than the growth-regulator juvenile hormone when tested against *Dysdercus similis* larvae.

The extract obtained from *Nigella sativa* seeds shows anti-inflammatory and anti-cancer effects, both in vivo and in vitro. Antifungal and anti-parasitic properties have also been reported, as it is also a depressant for the central nervous system, which translates into sedative and neuroprotector properties. On the other hand, the dichloromethane extract from the seeds has shown diuretic and hypotensive activity. Both the seeds and the oil extracted from them have shown to have hypoglycemic, gastric protective and hepatic protective, analgesic and anti-inflammatory activity (Al-Ghamdi M S. "The anti-inflammatory, analgesic and antipyretic activity of *Nigella sativa*." J Ethnopharmacol. 2001; 76:45-8; El-Dakhakhny M, Mady N J, Lembert N, Ammon H P. "*Nigella sativa* oil, nigellone and derived thymoquinone inhibit synthesis of 5-lipoxygenase products in polymorphonuclear leukocytes from rats." J Ethnopharmaco. 2002; 81:161-4).

The essential oil from seeds is active against Gram-positive bacteria (*Staphyllococous aureus, Bacilus subtilis*) and Gran-negative bacteria (*Escherichia coli, Pseudomonas aeruginosa*); as it also possesses antiparasitic (Mahmound M. R., H. S. El-Abhar and S. Saleh. "The effect of *Nigella sativa* oil against the liver damage induced by *Schistosoma* infection in mice." Journal of Ethnopharmacology. 2002. 79:1-11) and anticonvulsant activity. It also shows antitumor, antiplatelet (Enomoto S, et al., "Hematological studies on black cumin oil from the seeds of *Nigella sativa* L.", Biol Pharm Bull. 2001; 24:307-10.) and contraceptive activity. Many of the activities attributed to *Nigella sativa* seeds may rooted in their powerful antioxidant activity (Gilani A, Jabeen Q. and Khan M. "A review of medicinal uses and pharmacological activities of *Nigella sativa*." Pakistan Journal of Biological Science. 2004; 7 (4) 441-451; Gali-Muhtasib, Hala & El-Najjar, Nahed & Schhneider-stock, Regine. "The medicinal potential of black seed (*Nigella sativa*) and its components." Advances in Phytomedicine. 2005; 2. 133-153).

Seeds are very rich and diverse in their chemical composition, as they contain amino acids, proteins, carbohydrates, and fixed and volatile oils. Much of the pharmacological activities mentioned above have been attributed to the quinone constituents in the seed. In 1956, Chopra et al. discovered that thymoquinone (TQ) is the main active component of volatile black seed oil. Mahfouz and El-Dakhakhny ("Studies on the Egyptian *Nigella sativa* L. IV Some pharmacological properties of seeds active principle in comparison to its dihydro compound and its polymer." Arzneim Forsch (Drug Res Germ). 1965; 15:1227-9) were the first to isolate "niugellone" from *Nigella sativa* seed oil, using Girard's reagent. Nogellone was later found to possess antihistamine properties in relatively low concentrations. El-Dakhakhny ("Studies on the chemical constitution of the Egyptian *Nigella sativa* L. seeds. II: The essential oil." Planta Medica. 1963; 12:465-70) was able to isolate the constituent components of Nogellone seeds from their essential oil, among which TQ was subsequently reported to be the main component of the volatile oil. Furthermore, El-Dakhakhny found that the "nigellone" isolated earlier was a dimer of TQ, which was afterwards called dithymoquinone (TQ2). The latter compound was found to be formed through the photodimerization of TQ as a consequence of exposure to sunlight during separation and extraction of seed quinones El-Fatatry ("Isolation and structure assignment of an antimicrobial principle from the volatile oil of *Nigella sativa* L. seeds." Die Pharmazie 30 2 (1975): 109-11) reported the isolation of thymohydroquinone (THQ) from the volatile seed oil of *Nigella sativa*. A different study showed that the chemical composition of the *Nigella sativa* black seed contained fixed oil (30%) and volatile oil (average 0.5%, maximum 1.5%). Volatile oil contained 54% TQ and a large number of monoterpenes, such as p-cymene and a-pinene, TQ2 and THQ.

The TQ content in *Nigella sativa* seed oil samples, extracted from different sources, was measured by gas chromatography (GC) analysis and ranks between 0.13-0.17% w/v of the oil.

Finally, *Nigella sativa* seeds contain fixed oils and volatile oils, which have a high-content of quinones, unsaturated fatty acids, amino acids and proteins, as they also contain traces of alkaloids and terpenoids. Most of the studies on the biological effects of *Nigella sativa* have applied its raw extracts in different solvents; however, some studies worked with its active ingredients. Out of all the isolated components of *Nigella sativa* volatile oils, TQ has qualified as the main active ingredient and, therefore, it is the most studied of such components (Gali-Muhtasib, Hala & El-Najjar, Nahed & Schhneider-stock, Regine. "The medicinal potential of black seed (*Nigella sativa*) and its components." Advances in Phytomedicine. 2005; 2. 133-153).

On the other hand, the genus *Asclepias curassavica* is part of the Apocynaceae family. It's an American genus with around 150 species. 68 of which can be found in Mexico. The *Asclepias curassavica* species require well-drained soils, both rich in nutrients and with an acidic or slightly alkaline pH. It resists temperatures of 0° C., while its optimum winter temperature is 10° C. The blossom occurs in spring, and therefore it's the season when they need the most water. It blooms in hot, semi-warm, dry, temperate, subtropical and tropical climates located from sea level to 1900 meters above sea level, with abundant water availability. Therefore, it has been observed in vacant lands, near residential areas, roadsides and streams, related to Mangrove, Deciduous Tropical Forest, Sub-deciduous, Sub-evergreen and Evergreen, Xerophilous Scrub, Induced Pasture, Mountain Mesophilic Forest, Oak, Pine and Oak-Pine Mixed Forests (Fernández A. M. "Usos de las especies del género Asclepias L. (Apocinaceae, Asclepiadoideae)", información del herbario nacional de México, Mexu. Polibotánica. 2008; 25:151-171).

It is an evergreen, erect or decumbent shrub, with simple or sparse branching, ligneous at its lower part, and its height grows up to 1 m. Opposite, lanceolate or oblong-lanceolate leaves, with a 5-15 mm petiole and a 1-4×5-12 cm leaf blade, from acute to acuminate. Inflorescences in extra-axial and terminal sections. Calyx with narrow 2-3 mm lanceolate lobes. Corolla with red or purple lobes, ovate to oblong, reflections and an ~2 mm orange crown. Androecium with 5 stamens welded to the corolla at its base. Fruit in a fusiform follicle, length up to 12 cm, glabrous or tiny pubescence on it. Compressed reddish-brown seeds, ~6 mm in length. Blossom occurs from May through October. Even as it reproduces by seed only, its stump can re-sprout after the removal or loss of the aerial part. Entomogamous pollination, especially by Lepuidopterans that frequently feed on the flowers from this species. Its invasive plant nature and how it lures butterflies have earned it a common English name-butterfly-weed-. It prefers exposures to full sun and acidic or slightly alkaline substrates. Drought-tolerant. It is a thermophilic plant and thus vulnerable to salinity or frosts.

Blooming occurs in practically every month of the year but the coldest period (January), as flower density peaks in the summer. Isolated fruits can be observed most of the year, as density peaks between July and August. Seed dispersal also happens by anemochoria, enhanced by the thistledowns from which its vernacular name comes, while its incidence peaks in the summer. These are long-range dispersals, and therefore seeds can reach distant enclaves. As in other species, however, the blooming of young plants to create new stands is limited to locations that meet some conditions, such as water availability, mild climate, and absence or scarcity of competing species (Fernández H. J. y Jordano B. D. "La mariposa monarca Dannus plexippus (L., 1758) en el estrecho de Gibraltar (Lepidoptera: Danaidae)." SHILAP Revista de Lepidopterología. 2009; 37 (148) 421-438).

*Asclepias curassavica* contains β-sitosterol, saponins, glycosides, cardenolides and steroids, cardiac glycosides (calotropogenin, calotoxin, uscharidin and voruscharin, and 12 beta-hydroxyicalotrapin) (Ricciardi-Verrastro B., Torres a. M., Camargo F. J. and Dellacassa E. S. "Validación del uso tradicional de especies de Asclepias contra veneno de Bothrops diporus (yarará chica) en el Nordeste de Argentina." Boletin Latinoamericano y del Caribe de Plantas Medicinales y Aromáticas. 2016; 15(2): 112-121).

Latex contains a cysteine protease that accelerates blood clotting, process similar to thrombin.

Some of the biological activities and traditional applications of this plant are the antimicrobial, antioxidant and antipasmodic capacity, which may be a result of dotriacontane. Likewise, phytochemical studies on ethanolic extract demonstrated the presence of glucosides, phenols, saponins, steroids, tannins, terpenoids, proteins and amino acids in *Asclepias curassavica* L. (Shelke V. and Bhot M. GS-MS "Analysis of bio-active compounds in ethanolic extracto of leaf and stem of Asclepia curassavica L." Int. J. Pharma. Investigation. 2019; 9 (2) 67-70), components also identified in other solvents, such as methanol, chloroform, hexane, petroleum, resins, quinones, flavonoids, coumarins and oil (Hemadri R. S., Chakravarthi M., Chandrashekara K. N. and Naidu C. V. "Phytochemical screening and antibacterial studies on Leaf and root extracto of *Asclepias curassavica* (L.)." Journal of Pharmacy and Biological Sciences. 2012; 2 (1) 39-44).

Phytochemicals that consist of compounds with biological properties as identified by GC-MS (Gas Chromatography-Mass Spectrometry).

We should highlight the n-hexadecanoic acid, since it has the following properties: hypocholesterolemic, nematicide, pesticide, antiandrogenic and hemolytic, while it also inhibits 5-alpha reductase (Sujayil, T. K. and Dhanaraj, T. S. "Determination of Bioactive Compounds in Evolvulus alsinoides Leaf Extract using GC-MS Technique." Research Journal of Life Sciences, Bioinformatics, Pharmaceutical and Chemical Sciences. 2016; 2, 34-38). Other authors argue that *Asclepias curassavica* has 9,12 octadecadienoic acid, known for its anti-inflammatory, cancer preventive, hepaprotective, antihistamine, anti-acne, anti-arthritic, anti-coronary and anti-eczemic (Pooja S, Ekta M, Rekha M. "Identification of phytocomponents in the methanol extract of *Cuscuta reflexa* grown on *Nerium oleander* host plant through GC-MS analysis." Int J Pharm Bio Sci 2017; 8:478-83) properties.

2014 and 2016 reports on squalene, a triterpene (saturated fatty acid), stated that it had antitumor, immunostimulant and chemopreventive activity, in addition to lipoxygenase-inhibition properties (Anika et al., 2016). Subbaiyan et al, ("Preliminary phytochemical screening, antibacterial activity and gas chromatography and mass spectrum analysis of *Ceropegia bulbosa* Roxb. (Aclepiadaceae)." Int J Recent Adv Multidiscip Res 2015; 2:841-7), argued that stigmasterol possesses thyroid-inhibitory, diuretic, anti-asthma, hypoglycemic and progesterone precursor properties.

In regard to the effect on heart conditions, its benefits are attributed to the presence of camarina, a cardiotonic cardiac and arrhythmic cardiac glycoside, that also works as a stimulant of congestive heart failure. Its gamma-tocopherol activity grants it properties as a cardioprotective (Evellyn C G, Priscila N C, Santos S G. "Alpha-tocopherol and gamma-tocopherol concentration in vegetable oils." Food Sci Technol 2014; 34:379-85) and card-20 (22)-enol ide as cardiac stimulant (Subbaiyan B, Jagatheskumar S, Mahendran G, Thangapandian V. "Preliminary phytochemical screening, antibacterial activity and gas chromatography and mass spectrum analysis of *Ceropegia bulbosa* Roxb. (Aclepiadaceae)." Int J Recent Adv Multidiscip Res 2015; 2:841-7).

Likewise, it also contains compounds with a pharmacological potential to reduce blood glucose and cholesterol levels due to 2-Methylhexacosane (Kathua et al., 2016). Due to the potential of its compounds, *Asclepias curassavica* has a wide range of properties that can be exploited in different industries. E.g., 1,2-benzenedicarboxylic acid can be used to synthesize dyes and perfumes, cytidine works as a glutamatergic antidepressant drug and nucleoside molecule (Sujayil, T. K. and Dhanaraj, T. S. "Determination of Bioactive Compounds in Evolvulus alsinoides Leaf Extract using GC-MS Technique." Research Journal of Life Sciences, Bioinformatics, Pharmaceutical and Chemical Sciences. 2016; 2, 34-38).

Some other molecules that provide *Asclepias curassavica* with its properties are Neoftadiene, 9, 12, 15 Octadecadienoic acid, Benzene, 1,1 (1,2-dimethyl-1,2-ethanediol) bis-(R*, S*), and 1-Monooleoylglycerol trimethylsilyl ether (Shelke V. and Bhot M. GS-MS "Analysis of bio-active compounds in ethanolic extracto of leaf and stem of Asclepia curassavica L." Int. J. Pharma. Investigation. 2019; 9 (2) 67-70).

The following documents are the result of a search on the closest technique status.

The medicinal properties of different spices and herbs are known to us, as Srivastava, ("Extracts from two frequently consumed spices Cumin (*Cuminum cyminum*) and turmeric (*Curcuma longa*) inhibit platelet aggregation and alter eicosanoid biosynthesis in human blood platelets." Prostaglandins, leukotrienes, and essential fatty acids, 37 (1), 57-641989) states. U.S. Pat. No. 5,482,111, awarded to Rajko D. Medenica, uses *Nigella sativa* seed extracts to improve the immune system and regulate some types of cancer. U.S. Pat. No. 4,986,895, awarded to Grossman et al., is aimed at the use of water-soluble plant extracts in the treatment of viral skin infections. U.S. Pat. No. 5,178,865, awarded to Ho et al., addresses the use of Chinese herbal extracts in the in vitro treatment of HIV-related diseases. 56 herbal extracts were tested for anti-HIV activity using in vitro methods.

A different use of extracts, as stated by U.S. Pat. No. 5,178,865 around some vegetable extracts faculties to control viruses. The US patent application 2020/0397711 also argues for the implementation of various plants extracts in the creation of macroparticles to treat various infectious diseases; they even point out that COVID-19 can be diminished in such manner. The same patent argues that the use of plant extracts would prevent the dangerous drug resistance conventional medications can sometimes induce.

Notwithstanding, no synergistic composition similar to the one hereof was found. The present composition aids in the efficient treatment of respiratory diseases such as Covid-19, asthma, chronic obstructive pulmonary disease (COPD) and other diseases that attack endothelial cells and the proteins that constitute said cells, and alleviates symptoms caused by affectations in the structure and functionality of proteins attacked by respiratory, infectious, and allergic diseases.

SUMMARY OF THE INVENTION

According to an aspect of the present invention, a synergistic composition aids in the efficient treatment of respiratory diseases such as Covid-19, asthma, allergies, and other diseases that attack endothelial cells and the proteins that constitute said cells, and alleviates symptoms caused by affectations in the structure and functionality of proteins attacked by respiratory, infectious, and allergic diseases.

According to another aspect of the present invention, a synergistic composition aids in the alteration of cellular plasticity by modifying protein interactions, which leads to cell reprogramming and cell rearrangement, thus allowing to preserve health or restore all organic functions, if applicable.

According to still another aspect of the present invention, a synergistic composition stimulates and strengthens the immune system.

According to yet another aspect of the present invention, a vegetable synergistic composition is provided with compounds that enable the alteration of cellular microenvironment, thus facilitating a rearrangement of the proteins responsible of binding, transporting, and even defending cells, making its responsiveness towards the cell more effective and capable.

In addition to the attributes and aspects that will appear as the general and detailed outlines hereof unfold, relevant illustrations will accompany.

Research and tests were performed on separate extracts of the plants *Nigella sativa* and *Asclepias curassavica* in order to achieve a synergistic composition aimed at treating respiratory diseases and strengthening the immune system to fight different diseases, as shown in example 2 and FIG. 4 of the detailed description, in the gelatin test on the structure of protein amino acids.

Surprisingly, these studies found that a mixture of oil extracted from *Nigella sativa* seeds and an alcoholic extract with ethanol from *Asclepias curassavica* aerial parts, in addition to propylene glycol and ethanol as solvents to balance hydrogen bonds between said compounds and those from plant extracts, led to astonishing results when administered to patients with COVID-19 and other respiratory, infectious and allergic diseases, in opposition to such extracts being administered separately Propylene glycol and alcohol provide *Asclepias curassavica* aerial extracts and *Nigella sativa* seeds oil with molecular stability, as water/alcohol mixtures and diol-type aliphatic alcohols, such as propylene glycol, increase the aqueous solubility of some pharmaceutical forms, as this is an important interest for this industry.

The mixture of both extracts led to a synergistic effect that considerably reduces the symptoms and conditions caused by COVID-19 related to the SARS-COV-2 virus and other respiratory, infectious and allergic diseases.

The synergistic composition used to treat respiratory diseases, strengthen the immune system to fight other diseases, such as infectious and allergic diseases comprises of a synergistic mixture of oil extracted from *Nigella sativa* seeds and an alcoholic extract from *Asclepias curassavica* aerial parts, in addition to propylene glycol and ethanol as solvents to balance such extracts, which is described below.

The present invention is specifically aimed at a synergistic composition to treat diseases, such as COVID-19 caused by the SARS-COV-2 virus, that attacks endothelial cells, as well as other diseases that attack the proteins that constitute endothelial cells, in order to alleviate symptoms caused by affectations in the structure and functionality of proteins attacked by respiratory, infectious and allergic diseases with a synergistic mixture of oil extracted from *Nigella sativa* seeds and an alcoholic extract from *Asclepias curassavica* aerial parts, in addition to propylene glycol and ethanol as solvents to molecularly balance the compounds of such extracts, to subsequently modify proteins and prevent affectations in endothelial cells using a concentration that effectively alleviates symptoms (see example 2 of detailed outline).

Such synergistic composition used to treat respiratory diseases and strengthen the immune system to fight viral infections, such as COVID-19 caused by the SARS-COV-2 virus, other respiratory diseases and other infectious and allergic diseases, consists of a mixture of a) oil extracted from *Nigella sativa* seeds diluted in propylene glycol with b) alcoholic extract with ethanol from *Asclepias curassavica* aerial parts.

According to a preferred embodiment of the invention, oil extracted from *Nigella sativa* seeds is diluted in propylene glycol, 2 ml of oil per 1L of propylene glycol.

According to a preferred embodiment of the invention, alcoholic extract with ethanol of *Asclepias curassavica* aerial parts is obtained by macerating approximately 20-50 g of *Asclepias curassavica* aerial parts in 1 L of 96% ethanol via double boiler (10-15 min), letting it rest for 12-24 hours; you can also omit the double boiler process, letting it rest for 48-72 hours-strain and filter subsequently. *Asclepias curassavica* aerial parts are obtained from stems, unripe and/or mature follicles, flowers, dried or fresh leaves or mixtures thereof.

According to a preferred embodiment of the invention, the synergistic composition to treat respiratory diseases and fight viral infections, such as COVID-19 caused by the SARS-COV-2 virus, other respiratory diseases and infectious and allergic diseases in adolescent and adult patients comprises of a mixture of 500-900 ml of filtered alcoholic extract from *Asclepias curassavica* aerial parts with a 100-500 ml volume of oil extracted from *Nigella sativa* seeds in propylene glycol.

According to a preferred embodiment of the invention, the synergistic composition to treat respiratory diseases and strengthen the immune system to fight viral infections, such as COVID-19 caused by the SARS-COV-2 virus, other respiratory diseases and infectious and allergic diseases in child patients as per this invention comprises of a mixture of 500 of filtered alcoholic extract from *Asclepias curassavica* aerial parts with a 300-500 ml volume of oil extracted from *Nigella sativa* seeds in propylene glycol.

This invention also provides the use of a composition defined by a synergistic mixture of oil extracted from *Nigella sativa* seeds and an alcoholic extract from *Asclepias curassavica* aerial parts, in addition to propylene glycol and ethanol as solvents to balance such extracts into a safe and effective dose to alleviate symptoms and treat diseases such as COVID-19 and respiratory, infectious and allergic diseases.

The composition defined by a synergistic mixture of oil extracted from *Nigella sativa* seeds and an alcoholic extract from *Asclepias curassavica* aerial parts, in addition propylene glycol and ethanol as solvents to balance such extracts, alleviates the symptoms caused by affectations in the structure and functionality of proteins attacked by respiratory, infectious and allergic diseases, by administrating such composition as a safe and effective concentration (10 mg-50 mg of extracts). Effectiveness and safety are described in procedure 1, at a 44 µl-300 µl dose administered based on the disease and its severity (as described in procedures 1 and 4).

This invention also provides a remedy to activate cellular molecules, particularly proteins, to reactivate molecular activity (rearrangement of proteins that, as they alter their binding interactions, reactivate their activity; alterations in the microenvironment lead to new bonds in elastic proteins). Active principles are a composition comprising of a synergistic mixture of oil extracted from *Nigella sativa* seeds and an extract from *Asclepias curassavica* aerial parts, in addition to propylene glycol and ethanol as solvents to balance such extracts, by administrating such composition as a safe and effective concentration (10 mg-50 mg of extracts). Effectiveness and safety are described in procedure 1, at a 44 µl-300 µl dose administered based on the disease and its severity (as described in procedures 1 and 4).

This invention is also aimed at finding a method to diminish the side effects of vaccines administered to humans to control the SARS-COV-2 virus, by means of a safe and effective dose of a composition comprising of a synergistic mixture of oil extracted from *Nigella sativa* seeds and an extract from *Asclepias curassavica* aerial parts, in addition propylene glycol and ethanol as solvents to balance such extracts, by administrating such composition as a safe and effective concentration (10 mg-50 mg of extracts). Effectiveness and safety are described in procedure 1, at a 44 µl-300 µl dose (as described in procedures 1 and 4).

This invention also provides a method for alleviating the symptoms caused by SARS-COV-2 in infected humans from 6 months of age to senior citizens, pregnant women, disabled children and adults, comprising of the administration of a safe and effective dose made of a composition of synergistic mixture of oil extracted from *Nigella sativa* seeds and an extract from *Asclepias curassavica* aerial parts, in addition to propylene glycol and ethanol as solvents to balance such extracts, by administrating such composition as a safe and effective concentration (10 mg-50 mg of extracts). Effectiveness and safety are described in procedure 1, at a 44 µl-300 µl dose administered based on the disease and its severity (as described in procedures 1 and 4).

This invention is also aimed at finding a method to regenerate lung tissue affected by SARS-COV-2 in infected humans, comprising of the administration of a safe and effective dose made of a composition of synergistic mixture of oil extracted from *Nigella sativa* seeds and an extract from *Asclepias curassavica* aerial parts, in addition to propylene glycol and ethanol as solvents to balance such extracts, by administrating such composition as a safe and effective concentration (10 mg-50 mg of extracts). Effectiveness and safety are described in procedure 1, at a 44 µl-300 µl dose (as described in procedures 1 and 4).

Furthermore, this invention is aimed at finding a method to improve elastic proteins functions and restructuring in humans by administering a safe and effective dose made of a composition of synergistic mixture of oil extracted from *Nigella sativa* seeds and an extract from *Asclepias curassavica* aerial parts, in addition to propylene glycol and ethanol as solvents to balance such extracts, by administrating such composition as a safe and effective concentration (10 mg-50 mg of extracts). Effectiveness and safety are described in procedure 1, at a 44 µl-300 µl dose (as described in procedures 1 and 4).

This invention also provides a process to improve the microenvironment that protects normal cells of cytopathic effects caused by SARS-COV-2, comprising of the administration of a safe and effective dose made of a composition of synergistic mixture of oil extracted from *Nigella sativa* seeds and an extract from *Asclepias curassavica* aerial parts, in addition to propylene glycol and ethanol as solvents to balance such extracts, by administrating such composition as a safe and effective concentration (10 mg-50 mg of extracts). Effectiveness and safety are described in procedure 1, at a 44 µl-300 µl dose (as described in procedures 1 and 4).

Likewise, this invention provides a method to improve the cardio-respiratory capacity of human beings by administering a safe and effective dose made of a composition of synergistic mixture of oil extracted from *Nigella sativa* seeds and an extract from *Asclepias curassavica* aerial parts, in addition to propylene glycol and ethanol as solvents to balance such extracts, at the produce concentration necessary to improve cardio-respiratory capacity, by administrating such composition as a safe and effective concentration (10 mg-50 mg of extracts). Effectiveness and safety are described in procedure 1, at a 44 µl-300 µl dose (as described in procedures 1 and 4).

The composition of synergistic mixture of oil extracted from *Nigella sativa* seeds and an extract from *Asclepias curassavica* aerial parts, in addition to propylene glycol and ethanol as solvents to balance such extracts leads to an alteration in elastic protein structure by creating new bonds and altering the molecular microenvironment of cells, which in turns modifies cell plasticity (see example 2 of detailed outline).

The composition of synergistic mixture of oil extracted from *Nigella sativa* seeds and an extract from *Asclepias curassavica* aerial parts, in addition to propylene glycol and ethanol as solvents to balance such extracts helps to prevent elastin degradation in the alveoli, as caused by affectations produced by neutrophilia as a result of a SARS-COV-2 infection, since the tertiary structure of such proteins is modified, thus ensuring breathing capacity even in a situation of moderate lung damage.

As an elastic protein and the main covering protein, elastin is the main cause of damage to alveoli. Covid-19 causes infected patients to lose elasticity of these proteins, as low values in oximetry studies suggest, while oximetry values could improve by administering the composition described herein. To better understand the invention features, the following drawings are a component of the present outline as they are an integral part thereof. Drawings are explanatory without limitation.

BRIEF DESCRIPTION OF THE DRAWINGS

FIG. 1 features a chart with the percentage of subjects from groups 3 through 6 that showed possible Covid-19 symptoms.

FIG. 2 features a chart with the average condition of all subjects with Covid-19-related symptoms (groups 1 and 2 of the study hereof), in which total samples equal 200 (1% are hospitalized subjects with no invasive mechanical ventilation; 5% are hospitalized subjects with invasive mechanical ventilation; 36% are outpatients on no medication and 58% are outpatients on medication).

FIG. 3 features a comparison of the flour samples; A2 and A4 are flour samples with the synergistic composition to treat respiratory, infectious and allergic diseases, as per the present invention; A1 and A3 are flour samples without the synergistic composition of the present invention; B shows a Scanning Electron Microscopy image without the synergistic composition hereof, with no defined trabeculae and compact appearance, while C shows a Scanning Electron Microscopy image with the synergistic composition hereof that shows defined trabeculae (highlighted by arrows and rough appearance).

FIG. 4 features four Scanning Electron Microscopy (SEM) images of Gelatin samples at a X50SE magnification; in image A) GR1, water was added; in image B) GR2, alcohol with A. curassavica extract was added; in image C) GR3, propylene glycol with *N. sativa* was added; and in image D) GR4, the synergistic composition to treat respiratory, infectious and allergic diseases, as per the present invention, was added.

FIG. 5 features four Scanning Electron Microscopy (SEM) images of the Gelatin samples at a X500 magnification; in image A) GR1, water was added; in image B) GR2, alcohol with *Asclepias curassavica* extract was added; in image C) GR3, propylene glycol with *Nigella sativa* was added; and in image D) GR4 the synergistic composition to treat respiratory, infectious and allergic diseases, as per the present invention, was added.

FIG. 6*a* schematizes the collagen structure, as the first image features the amino acid sequences, the second one shows the sphere model of the helix, the third image portrays a 3-helix winding to form a chain known as tropocollagen, and lastly, a superhelix made of three collagen chains as represented by balls and rods FIG. 6*b* schematizes the Gelatin structure: 1. hydrolyzed collagen chain (cut or divided); 2. crease of the collagen chain; 3. 3D network.

FIGS. 7A, 7B and 7C feature images of the chest X-ray of a 57-year-old patient before contracting covid-19; two months after their discharge from the hospital and the first intake of the synergistic composition hereof; and six months in of continuously taking the synergistic composition, respectively.

FIG. 8 features a simple spirometry chart and a simple spirometry with salbutamol as A-quality bronchodilator from a 57-year-old patient with 80% Forced Vital Capacity (FVC). The dotted lines work as control parameters for subjects 8 to 20 years old (upper line) and 21 to 65 years old (lower line).

FIG. 9 features a simple spirometry chart and a simple spirometry with A-quality bronchodilator from a 57-year-old patient with 81% Forced Vital Capacity (FVC). The dotted lines work as control parameters for subjects 8 to 20 years old (upper line) and 21 to 65 years old (lower line).

FIG. 10 features the chest X-ray of a 30-year-old patient during their infection with SARS-COV-2 which led to the contagion of Covid-19.

FIG. 11 features a simple spirometry chart and a bronchodilator spirometry (salbutamol) of a 30-year-old patient with 87% Forced Vital Capacity (FVC). The dotted lines work as control parameters for subjects 8 to 20 years old (upper line) and 21 to 65 years old (lower line).

FIGS. 12A-12B features the chest X-ray of a 17-year-old woman who was administered the synergistic composition of this invention.

FIG. 13 features a simple Spirometry chart of a 71-year-old woman with lung age according to a 65-year-old person; highlighted in gray is the control parameter for subjects 8 to 20 years old (upper line of gray area) and for subjects 21 to 65 years old (lower line of gray area).

FIG. 14 features a simple Spirometry chart of a 47-year-old subject with no visible damage. Curves fall within the expected parameters while the gray lines are interrupted. The dotted lines work as control parameters for subjects 8 to 20 years old (upper line) and 21 to 65 years old (lower line).

FIGS. 15A-15B feature two chest X-rays from an 82-year-old male and a 33-year-old female, respectively, who were administered the synergistic composition of the present invention as both underwent a Covid-19 infection.

FIG. 16 features a Spirometry chart of an 82-year-old male that was discarded as the age exceeded the expected ranges. The curves continue outside the control area, highlighted in gray.

FIG. 17 features four different images of pulse oximeters that show the blood oxygen saturation readings of a subject who received the synergistic composition of the present invention, thus registering a continuous improvement after receiving the composition.

To better understand the present invention, some modalities hereof will be addressed in a detailed fashion below. Such outline is supported by illustrative but non-limiting drawings.

DETAILED DESCRIPTION OF THE INVENTION

The following outline and the attached drawings detail the unique features of the synergistic composition for treating respiratory diseases and fighting other diseases, and the method for preparing such composition; reference signs also serve to indicate such parts.

The synergistic composition to treat respiratory diseases and fight other diseases, such as infectious and allergic diseases, that comprises of a synergistic mixture of oil extracted from *Nigella sativa* seeds and extract from *Asclepias curassavica* aerial parts, in addition to propylene glycol and ethanol as solvents to balance such bonds through hydrogen bonds hydrogen bonds between said compounds and those from plants; such extracts are obtained as described below.

Preparation of Oil from *Nigella sativa* Seeds

Extract oil from *Nigella sativa* seeds resorting to the cold pressing method. Such oil contains approximately 1-2% of Thymoquinone; add 1-10 ml of oil and preferably 2 ml of oil per propylene glycol liter.

Alcoholic extract from *Asclepias curassavica* aerial parts

Method A

Add 20 g-50 g of *Asclepias curassavica* aerial parts in one liter of ethanol-preferably ethanol 96%-. Aerial parts are selected from 2-5 30 cm stems. Add follicles, 50% mature and 50% green; also add flowers and leaves of different sizes, both dry and green, and make sure the latter equal to approximately 40%-50% of the total weight of aerial parts. Double boil this mixture for approximately 10-15 minutes; let it cool and rest for 12-24 hours.

Method B

In 1 liter of ethanol 96%, add 15-21 g of leaves, as the specific amount depending on whether leaves are dry or fresh, large or small, and the season; add 4-7 g of follicles; 5-10.2 g of stems, specific amount also depending on the season and their thickness; and a gram of flowers; let it rest 48-72 hours. Filter the alcoholic extract from *Asclepias curassavica* aerial parts using a strainer and then pour it through a Grade 2 filter.

Different mixtures were produced to obtain the synergistic composition used to treat respiratory diseases and fight other diseases in adolescents and adults, as per the present invention. The mixture that provided the best results comprised of 500-900 ml of the filtered alcoholic extract from *Asclepias curassavica* aerial parts plus 90-150 ml of oil extracted from *Nigella sativa* seeds in propylene glycol. The mixture was shaken vigorously and then rested for 24 hours. It was subsequently bottled in 8 ml droppers.

500 ml of the filtered alcoholic extract from *Asclepias curassavica* aerial parts plus 300-500 ml of oil extracted from *Nigella sativa* seeds in propylene glycol were mixed to obtain the synergistic composition used to treat respiratory diseases and fight other diseases in child patients, as per the present invention. The mixture was shaken vigorously and then rested for 24 hours. It was subsequently bottled in droppers for dosage purposes.

A preferred embodiment of the invention features the administration of the synergistic composition hereof via the nasal, oral, sublingual, or anal route.

The composition may be administered to patients in addition to supplements, antibiotics, anticoagulants, immune modulators, glucocorticoids, analgesics, antipyretics, or a combination thereof.

The following are dosage methods for the synergistic composition to treat respiratory diseases and fight other diseases as per this invention: drops, capsule, tablet, granules, suppository, gel, and aerosol.

Dosage

Composition dose as established by the mixture of oil extracted from *Nigella sativa* seeds and an alcoholic extract from *Asclepias curassavica* aerial parts, in addition to propylene glycol and ethanol as solvents to balance such extracts.

During the experiments, the following doses were deemed as safe and effective to be administered to adolescents and adults:
  i) 1 drop in each nostril per day, from 3 to 15 weeks, preferably 3 to 5 weeks, to prevent respiratory diseases or those caused by viral infection.
  ii) 1 drop in each nostril for three days in a row; subsequently, 1 to 2 doses per week for 8 to 20 weeks in order to reduce symptoms, in the event of diseases caused by infection, such as the SARS-COV-2 in early stages, influenza, asthma, sinusitis, allergies and symptoms caused by vaccines such as Pfizer, AstraZeneca, Sputnik V or CanSino.
  iii) 1 drop in each nostril in the morning, plus 5 sublingual drops twice in the afternoon, and one more drop in each nostril at night, daily for 15 days. The foregoing helps to alleviate symptoms in subjects in need of oxygen or in a severe stage of SARS-COV-2 infection.
  iv) 1 drop in each nostril in the morning and in the evening, plus 5 sublingual drops in the afternoon. Apply one week before and two weeks after vaccination for an effective antibody generation.
  v) 1 drop in each nostril every other day for 2 months, in order to improve conditions or symptoms caused after contracting a SARS-COV-2 infection (post-Covid symptoms).

During the experiments, the following doses were deemed as safe and effective to be administered to minors:
  i) 10 drops diluted in 10 ml water per day, two days a week, to prevent respiratory diseases or those caused by viral infection in subjects aged 9-15 years; full period: 7 weeks.
  ii) 5 drops diluted in 10 ml water per day, two days a week to prevent respiratory diseases or those caused by viral infection in subjects aged 2-8 years; full period: 4 weeks.
  iii) 2 drops diluted in 10 ml water per day, two days a week to prevent respiratory diseases or those caused by viral infection in subjects aged 6-24 months; full period: 4 weeks.
  iv) 10 drops diluted in 10 ml water per day, every day to alleviate symptoms caused by illnesses caused by SARS-COV-2, influenza, asthma, sinusitis and allergies in subjects aged 9-15 years; full period: 5 days.
  v) 5 drops diluted in 10 ml water per day, every day to alleviate symptoms caused by illnesses caused by SARS-COV-2, influenza, asthma, sinusitis and allergies in subjects aged 2-8 years; full period: 5 days.
  vi) 2 drops diluted in 10 ml water per day, every day to alleviate symptoms caused by illnesses caused by throat infections and thrushes in subjects aged 6-24 months; full period: 4 weeks.

During the experiments, the following doses were deemed as safe and effective to be administered in subjects such as pregnant women or subjects with intellectual disabilities:
  i) 5 sublingual drops per day, three days a week to prevent respiratory diseases or those caused by viral infection; full period: 5-12 weeks.
  ii) 5 sublingual drops per day, every day to alleviate symptoms caused by infections such as SARS-CoV-2 virus, influenza, asthma, sinusitis and allergies, and symptoms caused by vaccines such as Pfizer, AstraZeneca, Sputnik V, CanSino, full period: 2-3 weeks.

The effective dose for each case will be accurately described in the following example section.

Example 1

Procedure 1

The following procedure was conducted to evaluate the usefulness and effectiveness of the composition hereof towards regulating the symptoms caused by the COVID-19 disease caused by the SARS-COV-2 virus:

Treatment

Invasive mechanical ventilation for 10 hospitalized subjects, each according to individual parameters related to the patient's weight and the degree of respiratory capacity damage, as per the Covid-19 patient treatment guidelines issued by the Government of Mexico in February 2020. Azithromycin 500 mg, broad-spectrum antibiotic for 5 days, Clarithromycin 500 mg, antibiotic for the respiratory tract, Paracetamol 500 mg, analgesic and antipyretic for fever control every 4 hours, Dexamethasone 8 mg, intramuscular, steroid, anti-inflammatory drug, one injection every 24 hours.

The protocol for administering the composition hereof to patients with symptoms of different severity without requiring hospital care was found to be 2 intranasal drops per day; i.e., one drop in each nostril, every day for 3 weeks; subsequently, three doses per week. In the event symptoms partially or fully alleviate, the dose decreases to 1-2 applications per week until 20 applications are performed.

The dose for asymptomatic or healthy patients consists of 2 intranasal drops per day, 3 days a week, until 15 applications are performed.

Dosages for patients infected with the new variants of SARS-COV-2 are constantly changing, as well as for the prevention of this very virus. It is not the same for other respiratory diseases.

Patients

The study population consisted of 600 volunteers; authorization in behalf of hospitalized patients was given by their families. Patients were divided in 6 clusters.

CLUSTER 1:100 patients infected with Covid-19, as tested by the Mexican health sector via laboratory.

CLUSTER 2:100 symptomatic patients (high fever, loss of smell and appetite, diarrhea, phlegm, and cough) related to SARS-COV-2, but contagion not confirmed.

CLUSTER 3:99 healthy, asymptomatic subjects, but highly exposed to contagion as they are public health employees.

CLUSTER 4:100 subjects highly exposed to contagion as someone in their families or social circles tested positive for Covid-19.

CLUSTER 5:100 subjects highly exposed and ill with chronic respiratory diseases (asthma, rhinitis, sinusitis, bronchitis, smokers, allergies and loss of smell due to work-related inhalation of toxins).

CLUSTER 6:101 healthy subjects with a low risk of contagion, no comorbidities, no family members infected with Covid-19, athletic constitution and aged under 45 years.

Statistic

IBM SPSS Statistics 27.0 was used.

Results 1

Propylene glycol and alcohol provide *Asclepias curassavica* aerial extracts and *Nigella sativa* seeds oil with molecular stability, as water/alcohol mixtures and diol-type aliphatic alcohols, such as propylene glycol, increase the aqueous solubility of some pharmaceutical forms, as this is an important interest for this industry.

The macroscopic properties of these mixtures have been studied thoroughly, but there are certain limitations in how we understand the structural and energetic features of possible interactions rooted at the nanometric level. Thanks to computer designs, we know that hydrogen bonds are the main interaction forces that lead to the formation of clusters and their influence on measurable macroscopic properties for such mixtures.

In addition to interactions within mixtures, such interactions reportedly induce the mixture features while they also affect their activity towards an alteration of the microenvironment at the time of their implementation.

Based on how diol/water/alcohol mixtures interact, the mixture used in the present invention was therefore analyzed. Firstly, the specific case of the dose for respiratory diseases in preliminary studies shown in example 2 from which the minimum dose to alter the formation of elastic protein structures, such as glutenins, elastin and collagen, were obtained. Subsequently, and observing cluster knowledge, a single 10-drop dose was administered in a nostril of healthy subjects. Immediate reactions were analyzed; as no adverse reactions were observed 10 minutes after the administration, the subjects were monitored for a couple of weeks; as no adverse reactions were further observed, the study was conducted with a minimum dose. Due to previous studies, we know there is an alteration in the microenvironmental, which is the purpose of using approximately 20 μl of water/diol/alcohol solution.

A study was conducted on the effect of synergistic composition used to treat respiratory diseases and fight viral infections such as COVID-19 caused by SARS-COV-2, and other respiratory, infectious and allergic diseases, comprising of a mixture of a) oil extracted from *Nigella sativa* seeds diluted in propylene glycol with b) alcoholic extract with ethanol from Asclepia curassavica aerial parts. Such study was performed on a total of 600 subjects, of which 348 were male and 252 female; the average age was 44.27 years, as ages ranged from 20 to 78 years.

The antibiotics azithromycin was administered to 76% of patients who tested positive for COVID-19; 10% of symptomatic, but not tested, patients were also given this antibiotic; in addition to this antibiotic, 88 subjects from cluster 1 took paracetamol 500 mg every 4 hours, while 40% of subjects from cluster 2 received this analgesic and antipyretic to alleviate some symptoms related to Covid-19. Furthermore, it is worth noting that a subject from cluster I was given antibiotic clarithromycin 500 mg, while a second subject from the same cluster took 8 mg intramuscular dexamethasone. The rest of the subjects (472) of cluster 2, plus all subjects from clusters 3 to 6 did not take medication to alleviate symptoms related to Covid-19.

90% of patients in clusters 1 and 2 reported the following symptoms: fever, headache, cough, asthenia, anosmia and ageusia to different degrees of severity. 10% of patients only reported anosmia and ageusia, but such loss of smell was not associated to SARS-COV-2 as there were no other symptoms (table 1).

TABLE 1

Most common symptoms related to Covid-19 and incidence proportion in Clusters 1 and 2.

| SYMPTOMS | Cluster 1 | Cluster 2 |
| --- | --- | --- |
| High fever over 40° C. | 100% | 89% |
| Shortness of breath (dyspnea) | 100% | 70% |

TABLE 1-continued

Most common symptoms related to
Covid-19 and incidence proportion in Clusters 1 and 2.

| SYMPTOMS | Cluster 1 | Cluster 2 |
|---|---|---|
| Headaches | 100% | 90% |
| Body aches | 99% | 80% |
| Dry cough episodes | 100% | 90% |
| Asthenia | 100% | 95% |
| Anosmia | 100% | 100% |
| Ageusia | 100% | 100% |
| Vomiting | 70% | 30% |
| Diarrhea | 60% | 40% |

As drops of the composition hereof were applied to the nostrils, all subjects immediately presented one or more reactions of those listed in table 2. Other reactions also occurred, but were only detected by some of the members from both clusters, and therefore were discarded. The following reactions were shown mainly by patients who tested positive for Covid-19 and sporadically by non-tested patients, while asymptomatic clusters did not report a single case: low-grade fever, diarrhea, and low blood sugar levels.

TABLE 2

Percentage of subjects and reactions reported in each cluster
during the administration of drops of this invention.

| Symptoms reported when administering the drops of this composition | Cluster 1 (%) | Cluster 2 (%) | Cluster 3 (%) | Cluster 4 (%) | Cluster 5 (%) | Cluster 6 (%) |
|---|---|---|---|---|---|---|
| Nose burning | 185 | 80 | 80 | 80 | 81 | 79 |
| Tears | 75 | 71 | 60 | 60 | 60 | 59 |
| Runny nose | 80 | 70 | 49 | 51 | 52 | 49 |
| Cough (dry or wet) | 95 | 85 | 34 | 34 | 35 | 33 |
| Headache and/or dizziness | 80 | 60 | 6 | 8 | 11 | 5 |
| Sneezing | 100 | 90 | 10 | 10 | 11 | 9 |

Subsequently, these reactions were analyzed to determine if they occurred due to the application of the drops of the composition hereof or were rather related to the respiratory disease or distress afflicting the different subjects. Reactions, such as burning, tears, runny nose and cough were present in many subjects from all clusters. Cohen's Kappa coefficient was performed to determine if data prepared by two groups of researchers (homeopathic doctors and researchers) were not obtained randomly, while the Landis-Koch scale (1977), frequently used to qualitatively measure researcher agreements (Table 3), was also considered.

According to Landis and Koch, (1977) the Kappa coefficient of agreement of the two groups of researchers for each study group is nearly perfect, since it falls in the range specified in Table 3; it is worth noting that in the present study each group of researchers separately screened nearly 50 different subjects for each group, after which, the data compiled was added up to a total of all the subjects observed, using the 1 score for those who had had certain reaction and 0 for those responses that did not include such reaction, obtaining as a first output the percentages shown in Table 2.

TABLE 3

Evaluation of Kappa coefficient (Landis and Koch, 1977).

| 0.00 | Negligible |
|---|---|
| 0.01-0.20 | Slight |
| 0.21-0.40 | Just |
| 0.41-0.60 | Moderate |
| 0.61-0.80 | Substantial |
| 0.81-1.00 | Nearly perfect |

The remarks made by the two research groups are in agreement regarding that the composition of the present invention elicits reactions in all study groups, being nearly perfect for Groups 1 and 2 (Table 4), which are the groups where subjects with symptoms related to Covid-19 are clustered, having the lowest values for Kappa, for the group of subjects considered to be at high risk (Group 4) since they work in the healthcare sector, and the group considered to be at low risk, consisting of healthy subjects (Group 6); all values are in the nearly perfect range, according to Table 3.

TABLE 4

Intra-researcher agreement, Kappa test, by study group.

| Group 1 | 1 (100%) |
|---|---|
| Group 2 | 1 (100%) |
| Group 3 | 0.947 (94.7%) |
| Group 4 | 0.96 (96%) |
| Group 5 | 0.954 (95.4%) |
| Group 6 | 0.947 (94.7%) |

In Table 5, values were obtained for each reaction by study group, with values in the ranges of nearly perfect agreement in most of the groups for each reaction, having values of considerable in the reaction of tearing and headache for Group 5 and moderate in headache for Group 6.

TABLE 5

Inter-researcher agreement, Cohen's Kappa test for reactions to administration
or dosage of the composition of the present invention by study group.

| | Group 1 | Group 2 | Group 3 | Group 4 | Group 5 | Group 6 |
|---|---|---|---|---|---|---|
| Nose burning | 0.866 (86.6%) | 0.925 (92.5%) | 0.935 (93.52%) | 0.968 (96.8%) | 10.935 (93.5%) | 1 (100%) |
| Tearing | 0.896 (89.6%) | 0.942 (94.2%) | 0.979 (97.9%) | 1 (100%) | 0.650 (65%) | 1 (100%) |
| Headache and/or dizziness | 1 (100%) | 0.920 (92%) | 0.847 (84.7%) | 0.826 (82.6%) | 0.754 (75.4%) | 0.597 (59.7%) |
| Severe sneezing | 1 (100%) | 0.834 (83.1%) | 0.889 (88.9%) | 0.947 (94.7%) | 1 (100%) | 0.942 (94.2%) |
| Cough | 0.904 | 0.987 | 1 | 0.976 | 0.976 | 1 |

TABLE 5-continued

Inter-researcher agreement, Cohen's Kappa test for reactions to administration or dosage of the composition of the present invention by study group.

|  | Group 1 | Group 2 | Group 3 | Group 4 | Group 5 | Group 6 |
|---|---|---|---|---|---|---|
| (phlegm or dry) | (90.4%) | (98.7%) | (100%) | (97.6%) | (97.6%) | (100%) |
| Nasal drip | 0.884 (88.4%) | 0.911 (91.1%) | 0.939 (93.9%) | 0.940 (94%) | 0.960 (96%) | 0.980 (98%) |

The researchers teams were comprised by 3 homeopathic physicians in the first team, and 3 researchers in the second team; subsequently we proceeded to determine whether there was a correlation of the reactions associated with the presence of the SARS-COV-2 virus or whether they were considered side effect reactions of the composition of the present invention, with no relevance to the health problems presented by the patients, so we proceeded to perform Pearson's correlation test to find out if there was any correlation (Table 6).

TABLE 6

Pearson correlation between each study group.

|  | Groups 1/2 | Groups 1/3 | Groups 1/4 | Groups 1/5 | Groups 1/6 | Groups 2/3 | Groups 2/4 | Groups 2/4 | Groups 2/6 |
|---|---|---|---|---|---|---|---|---|---|
| Nose burning | 0.932 (93.2%) | 0.873 (87.3%) | 0.901 (90.1) | 0.967 (96.7%) | 0.867 (86.4%) | 0.937 (93.7%) | 0.967 (96.7%) | 0.967 (96.7%) | 0.934 (93.4%) |
| Tearing | 0.903 (90.3%) | 0.702 (70.2%) | 0.737 (73.7%) | 0.816 (81.6%) | 0.693 69.3%) | 0.740 (74%) | 0.740 (74%) | 0.745 (74.5%) | 0.693 (69.3%) |
| Headache and/or dizziness | 0.733 (73.3%) | 0.478 (47.8%) | 0.488 (48.8%) | 0.459 (45.9%) | 0.451 (45.1%) | 0.665 (66.5%) | 0.626 (62.6%) | 0.652 (65.2%) | 0.622 (62.2%) |
| Severe sneezing | 0.631 (63.1%) | 0.130 13%) | 0.152 (15.2%) | 0.181 (18.1%) | 0.118 (11.8%) | 0.206 (20.6%) | 0.241 (24.1%) | 0.287 (28.7%) | 0.187 (18.7%) |
| Cough (phlegm or dry) | 0.559 (55.9%) | 0.059 (5.9%) | 0.059 (5.9%) | 0.062 (6.2%) | 0.045 (4.5%) | 0.105 (10.5%) | 0.105 (10.5%) | 0.105 (105%) | 0.094 (9.4%) |
| Nose drip | 0.579 (57.9%) | 0.181 (18.1%) | 0.181 (18.1%) | 0.185 (18.5%) | 0.163 (16.3%) | 0.313 (31.3) | 0.313 (31.3%) | 0.320 (32%) | 0.299 (29.9%) |

With the Pearson's values (Table 6), it can be noted that the burning and tearing are exclusively a result of the intranasal application of drops of the composition of the present invention, since there is a highly significant correlation in each group for such reactions, i.e., this reaction is similar both in Group 1 and 2 patients, as well as in healthy patients (Group 3 to 6). In the case of tearing, the correlation between Groups 3 to 6 (considering groups in preventive status) shows values with moderate significance regarding the group of patients confirmed with Covid-19, presenting a better significance with the group of non-confirmed patients, but with all the symptoms of this disease, reason for which, it is found in the possibility that nasal flow is imparted by the action of the composition droplets of the present invention; but it will depend on the disease severity for the abundance of nasal flow or another respiratory disease to occur, since within the Groups 3 to 6 there are subjects with other diseases of this kind, it is worth mentioning that even within the group of healthy people, there is evidence that when the drops are applied, they improve their breathing. Drops of the composition of the present invention are advised for all subjects of Groups 1 and 2, a daily application during three consecutive days, and subsequently two weekly applications until completing 20 doses.

For Groups 3 through 6, drops of the composition of present invention were applied at one drop per nostril per day per week; at the beginning, we made modifications after the second week since some subjects reported the appearance of symptoms related to Covid-19 (FIG. 1), the dose was changed to one drop per nostril per day during three days a week until 14 doses were completed, and the symptoms disappeared in the second week of application.

All 100% of subjects with both confirmed and unconfirmed Covid-19 symptoms started the application of the drops with the composition of the present invention between 4 to 17 days after the onset of the first symptoms, i.e., one drop per nostril per day for 3 consecutive days, and subsequently three times a week until completing 3 to 5 weeks. 12 of the subjects began taking the drops hospitalized or at hospital discharge; FIG. 2 presents the percentage of all subjects with Covid-19-related symptoms (study Groups 1 and 2) and their status during the present study.

Eight subjects received the drops of the composition of the present invention in the hospital, one drop in each nostril per day, until their health condition improved; these subjects presented Acute Respiratory Distress Syndrome (ARDS), as well as early onset of Chronic Obstructive Pulmonary Disease (COPD), with SpO2 values below 40%. At the time of the administration of the drops of the composition of the present invention, all 8 patients no longer required mechanical ventilation from the first intake, even one of the 3 women reported that ventilation was withdrawn minutes after the application of the drops; all patients were discharged without any complications, with SpO2 values above 90%.

There were 2 patients on invasive mechanical assistance, but the drops were not administered during their hospitalization, rather after it, they were hospitalized during 17 days, being 2 male subjects with ages of 38 and 57 years old, the subject with 38 years old did not present any evident damage; however, he was discharged with oxygen-mask support, and suffered extreme weakness and persistent dry cough that prevented him from resting; at the moment of the application of the drops of the composition of the present invention, being one drop in each nostril three times a day for 8 weeks, the oxygen-mask support was withdrawn, and he expelled phlegm with copious nasal flow, that allowed him to improve his breathing and the recurrent dry cough disappeared after the 3rd week. The 57 year-old patient was discharged with pulmonary microthrombosis and cerebral hypoxia, maintaining SpO2 values below 90% and extreme weakness that prevented him from walking and even sitting up in bed; at the time of use of the drops of the composition of the present invention, being one drop in each nostril three days a week, he did not require oxygen-mask support, his blood oxygen levels increased to 90%, weakness and persistent dry cough diminished within a week after the drops application; it is worth noting that this subject has begun to take his first steps with assistance, and the application of the drops will be extended.

Two subjects who received the drops at the aforementioned dose for patients with COVID prior to hospitalization were a couple aged 64 years for the female and 67 years for the male; the first one to be hospitalized was the male, who was administered with the drops only once four days before being hospitalized, the reason for the application was the presence of influenza symptoms, he discontinued its application, and was subsequently hospitalized; during his hospitalization he did not require invasive mechanical ventilation and during the 14 days of his hospitalization he received the drops of the composition of the present invention only once at the dosage mentioned above; at the time he was transferred to another hospital when it was confirmed that he suffered from Covid-19, and due to the protocols in place in the public healthcare sector, it was not possible to apply the drops; at the time he discontinued them, his SpO2 decreased to 70%, despite that, he did not require invasive ventilation support (only an oxygen-mask); upon discharge, he returned to the application of the drops at the aforementioned dose of one drop per nostril three times a week, maintaining an SpO2 between 92% and 96%, phlegm expulsion and abundant nasal flow, improving his breathing capability, and completely eliminating fever and general discomfort after 3 weeks of administration. The female patient, at the moment her husband was hospitalized, started treatment with azithromycin for 5 days, and subsequently started the administration of the drops with the composition of the present invention; she was hospitalized by the 4th day of the drops administration, the application of the drops was withdrawn, lowering her SpO2 to 80%, however, she did not require invasive ventilation and she remained hospitalized during 7 days, She resumed the drops administration after her release from the hospital and after the 14th application of the drops she received medical discharge.

The remaining Covid-19 positive subjects experienced improvements, in some cases almost immediately, 60% of the subjects mentioned that they felt improvement from the first application, and despite the fact that the fever persisted in almost 80% of them, they all reported that the weakness and shortness of breath had disappeared.

In Group 2, all subjects improved immediately, and those who presented severe symptoms felt their improvement between the 5th and 8th administration.

Groups 3 to 6, regardless of the 13 subjects who reported symptom onset (Graphic 1), were all found with no symptoms or discomfort.

Example 2

Procedure 2

Scanning Electron Microscopy

In order to assess the suitability of the composition of the present invention in the modification of the structures formed by elastic proteins, the following procedure was performed:

a) Wheat Flour

Two treatments were performed:
1) in the first one, a tablet was prepared with 25 g of wheat flour, adding 100 ml of water, 0.5 g of salt, 0.5 g of sugar and 2 drops of the composition of the present invention, and a control tablet without the composition of the present invention, stirred at room temperature for 15 min in a Thermo Scientific® digital stirrer, and dried in a Memmert® oven at 65° C. for 1 hour and at 37° C. for 12 hours. Subsequently, they were soaked with gold in the Delton Vacumm DeskV apparatus for microstructural characterization by means of a JEOL-brand scanning electron microscope-model JSM-7000F (7800F)—and its elemental analysis by EDS (Energy Dispersive Spectrometry).
2) The second treatment was performed as described above, except for the addition of 0.5 g of salt and 0.5 g of sugar.

b) Gelatin

Five mixtures were prepared in which, after weighing the water, the drops corresponding to each mixture were added, stirring for 15 seconds, immediately, the K'NOX® brand gelatin powder was added and mixed until a slurry was achieved, it was dried at room temperature for 48 hours and lyophilized for subsequent analysis.

GR1) 10 g of water+3 g of gelatin+10 drops of water
GR2) 10 g of water+3 g of gelatin+10 drops of alcohol with *A. curassavica* extract
GR3) 10 g of water+3 g of gelatin+10 drops propilenglicol with *N. sativa* extract.
GR4) 10 g of water+3 g of gelatin+10 drops of the synergistic composition for the treatment of respiratory, infectious-contagious and allergic diseases in accordance with the present invention.

Results 2

The samples obtained for this study were tested at the Universidad Autónoma de Ciudad Juárez.

FIG. 3 shows a comparison of the flour samples with and without the synergistic composition to treat respiratory diseases and strengthen the immune system against other diseases according to the present invention; A2 and A4 are flour samples with the synergistic composition to treat respiratory diseases and strengthen the immune system against other diseases according to the present invention; A1 and A3 are flour samples without the synergistic composition of the present invention; B shows a Scanning Electron Microscopy image without the synergistic composition of the present invention; and C shows a Scanning Electron Microscopy image with the synergistic composition of the present invention.

It should be noted that the 10 drops used in this study are approximately 220 µl, which clearly show the effects on protein interactions at microscopic level; however, concentrations ranging from 5 µl to 220 µl were used, and it is from 42 µl where slight or almost imperceptible changes can be observed, therefore, 10 drops were applied, but in some patients we started from two drops (around 44 µl), but only because these were applied several times, so it was stated as a baseline concentration in patients.

In Sample C, defined trabeculae are observed (pointed with an arrow) and the appearance is rough, not smooth as in sample A, which are the structures that compose the elastic proteins and form some sort of grid, known as gluten, while the sample without the synergistic composition to treat respiratory diseases and strengthen the immune system against other diseases according to the present invention, is distinguished by the fact of not presenting a grid, therefore, the trabeculae are absent.

FIG. 3A shows no visible difference between the 4 forms of bread with and without the synergistic synergistic composition to treat respiratory diseases and strengthen the immune system against other diseases according to the present invention, the 4 forms are the same; when looking at the forms shown in FIGS. 3B and 3C, it is possible to observe the changes at the molecule level due to the changes in the bonds presented by the proteins that conform the gluten, which is the grid that gives the characteristics of a mass.

According to FIG. 4, to determine the effect of the combination of the *A. curassavica* and *N. sativa* extracts, as well as the microenvironment generated by both the alcohol (ethanol) and propyleneglycol over the structure formed by the amino acids that form gelatin, we proceeded to perform tests, where the control used was water (GR1), and subsequently alcohol with *A. curassavica* extract (GR2), propyleneglycol with *N. sativa* (GR3) and the synergistic composition to treat respiratory diseases and against other diseases, in accordance with the present invention (GR4).

In FIG. 4, it can be observed in the electron microscopy that the change required for the collagen that composes the gelatin mainly forms the structure of trabeculae, is the one required for the collagen that composes the gelatin to form a structure of trabeculae, i.e., form a grid that allows a larger elastic capability and a higher capacity to adapt to environmental conditions; as can be observed in FIG. 4D, the grid exhibits defined trabeculae, as compared to the control (GR1) where no trabeculae are observed; it is a homogeneous lamina without a defined grid.

Whereas in the samples where only part of the composition of the present invention is present, the friable form observed in the control is not present, there is presence of trabeculae, but not as in the complete composite. This is more evident at higher magnification in FIG. 5D.

As can be observed in FIG. 5D, the structure promoted by the synergistic composition to treat respiratory diseases and against other diseases in accordance with the present invention, is a homogeneous, elastic grid; as it is well known, gelatin is formed by the hydrolysis of the collagen that composes bones, skin, or nerves, which are the structures mainly used to obtain this compound; collagen has a high concentration in all human organs, with high percentages by weight of tissue in some of the most representative human tissues and organs: 74% in skin, 64% in cornea, 50% in cartilage, 23% in whole cortical bone, 12-24% in aorta, 10% in lung and 4% in liver.

It is worth mentioning that the collagen in the gelatin is disrupted by the process of acid or alkaline hydrolysis, depending on the type of gelatin, and as can be observed in FIG. 5D, in the synergistic composition to treat respiratory diseases and strengthen the immune system against other diseases according to the present invention, it manages to form a grid again; although in the other Figures a lamina is observed, the trabeculae are not clearly distinguishable, indicating that the structure was not restored as with the composition of the present invention; there is an effect of both alcohol with *Asclepias curassavica* and propyleneglycol with *Nigella sativa*, but it is the complete formula the one that achieves the intended effect, and what we expect in order to obtain the expected results to improve the effects of different diseases.

TABLE 7

Amino acids of gelatin and residues composition in collagen per 1000 residues (Schrieber and Gareis 2007).

| Amino acid | Gelatin Type A | Gelatin Type B | Collagen Type 1 |
|---|---|---|---|
| Alanine | 112 | 117 | 114 |
| Arginine | 49 | 48 | 51 |
| Asparagine | 16 | 0 | 16 |
| Aspartic acid | 29 | 46 | 29 |
| Cysteine | — | — | — |
| Glutamic acid | 48 | 72 | 48 |
| Glutamine | 25 | 0 | 25 |
| Glycine | 330 | 335 | 332 |
| Histidine | 4 | 4.2 | 4.4 |
| Hydroxyproline | 91 | 93 | 104 |
| Hydroxylysine | 6.4 | 4.3 | 5.4 |
| Isoleucine | 10 | 11 | 11 |
| Leucine | 24 | 24.3 | 24 |
| Lysine | 27 | 28 | 28 |
| Methionine | 3.6 | 3.9 | 5.7 |
| Phenylalanine | 14 | 14 | 13 |
| Proline | 132 | 124 | 115 |
| Serine | 35 | 33 | 35 |
| Threonine | 18 | 18 | 17 |
| Tryprophan | — | — | — |
| Tyrosine | 2.6 | 1.2 | 4.4 |
| Valine | 26 | 22 | 22 |

Figure 1:
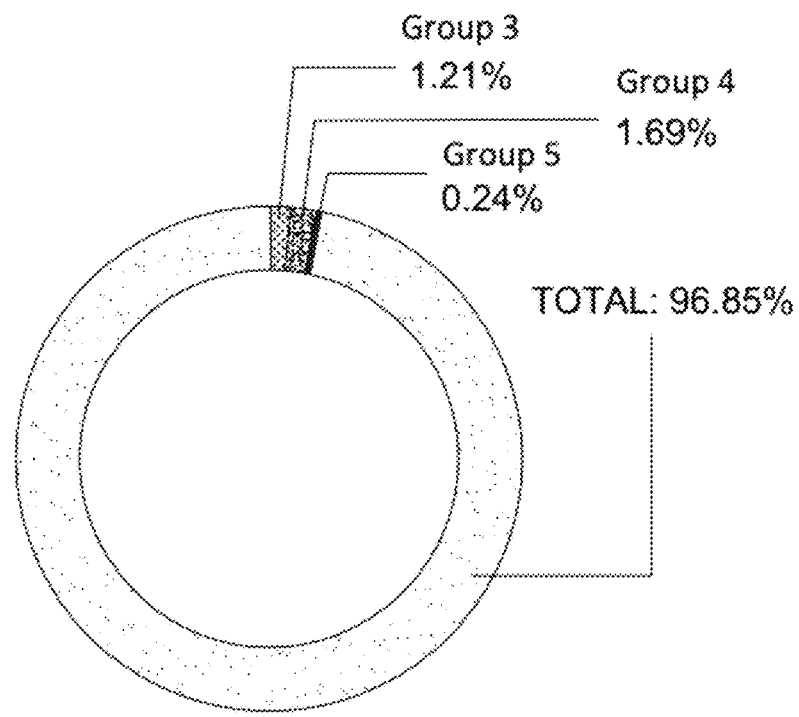
Figure 2:
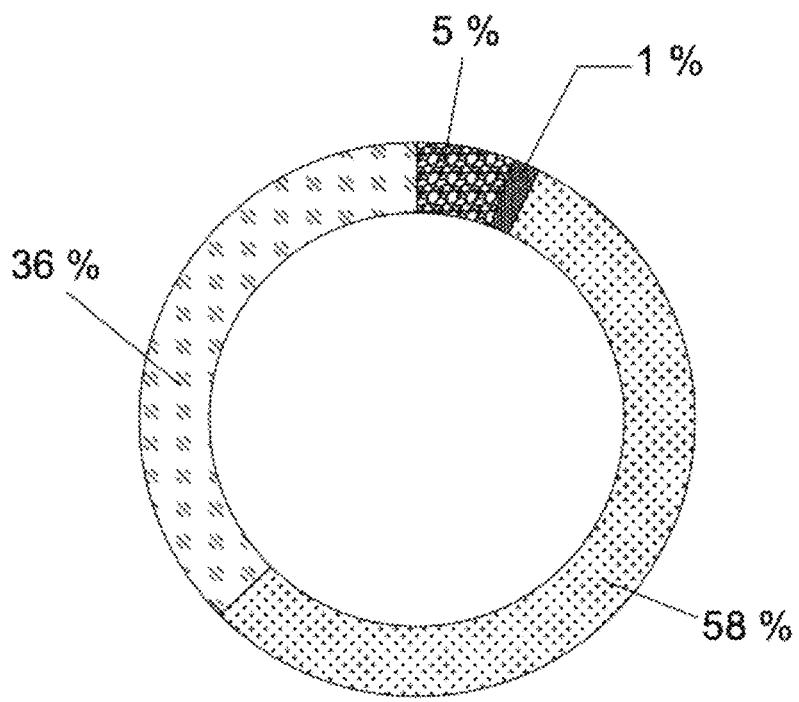
Figure 3:
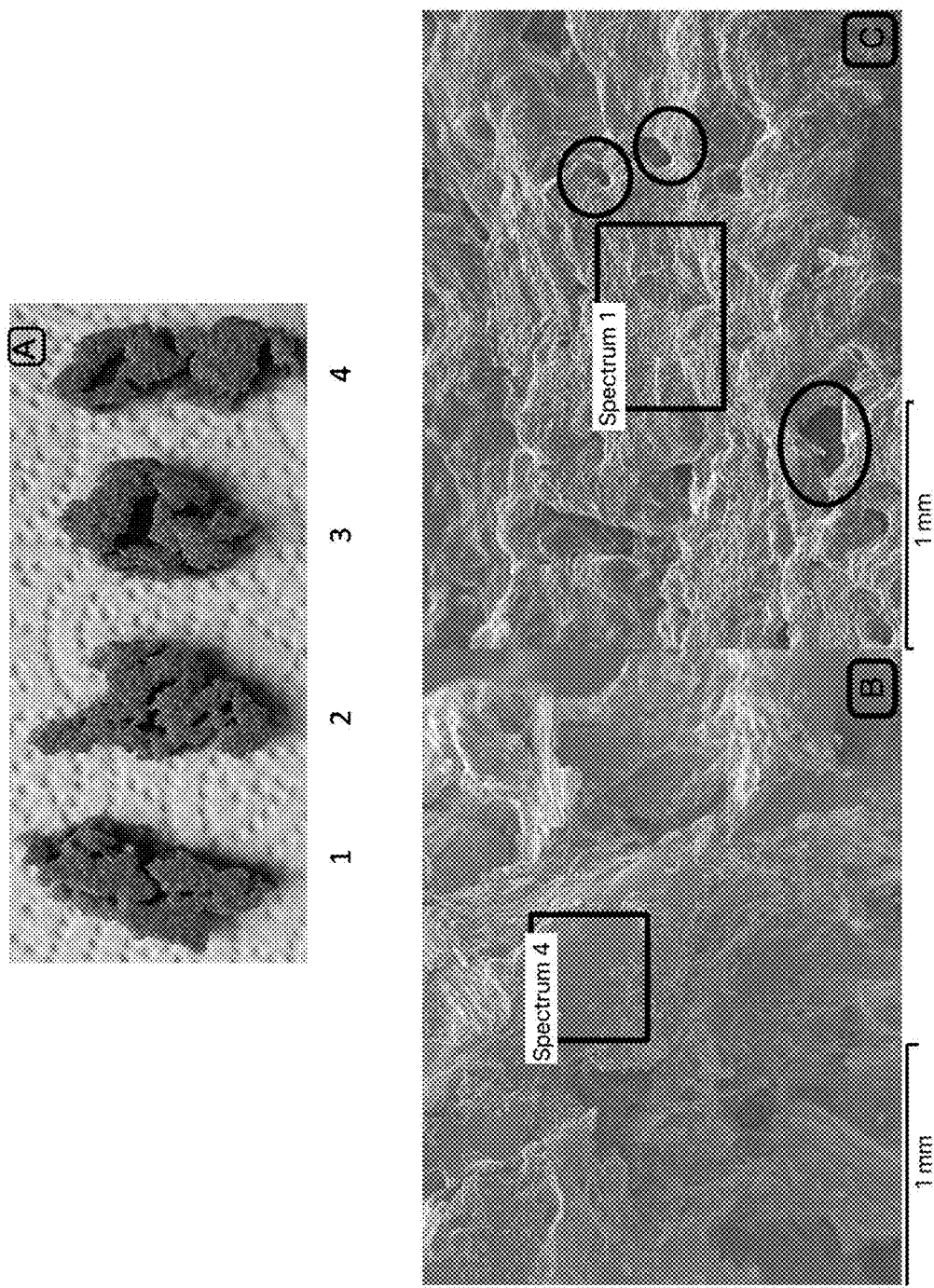
Figure 4:
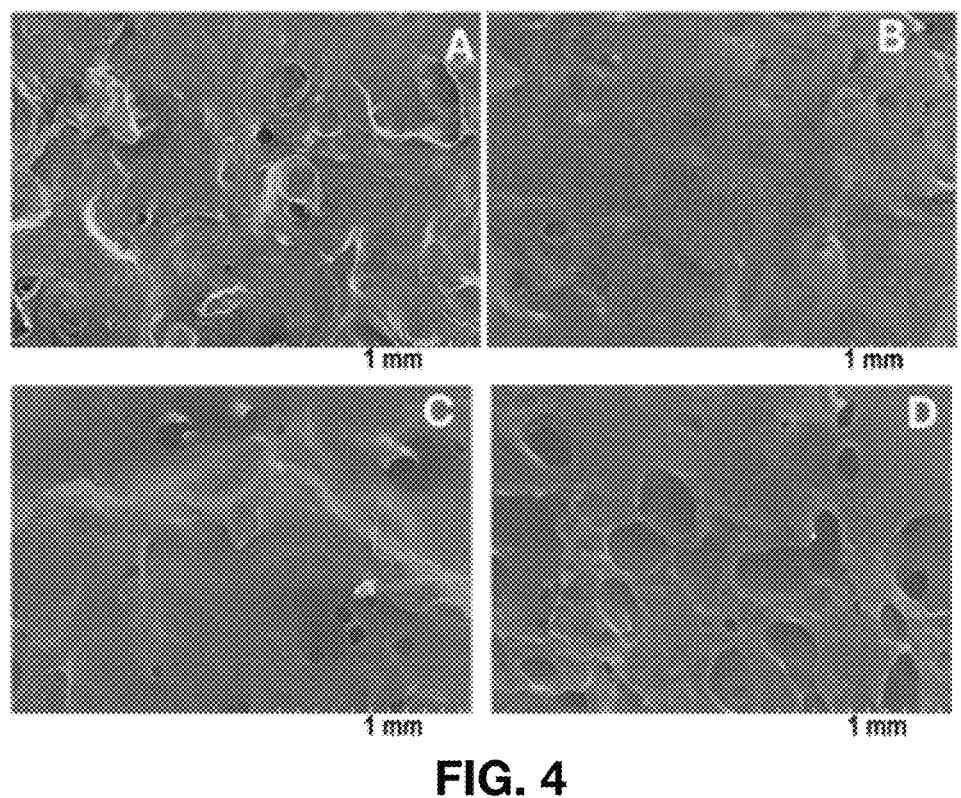
Figure 5:
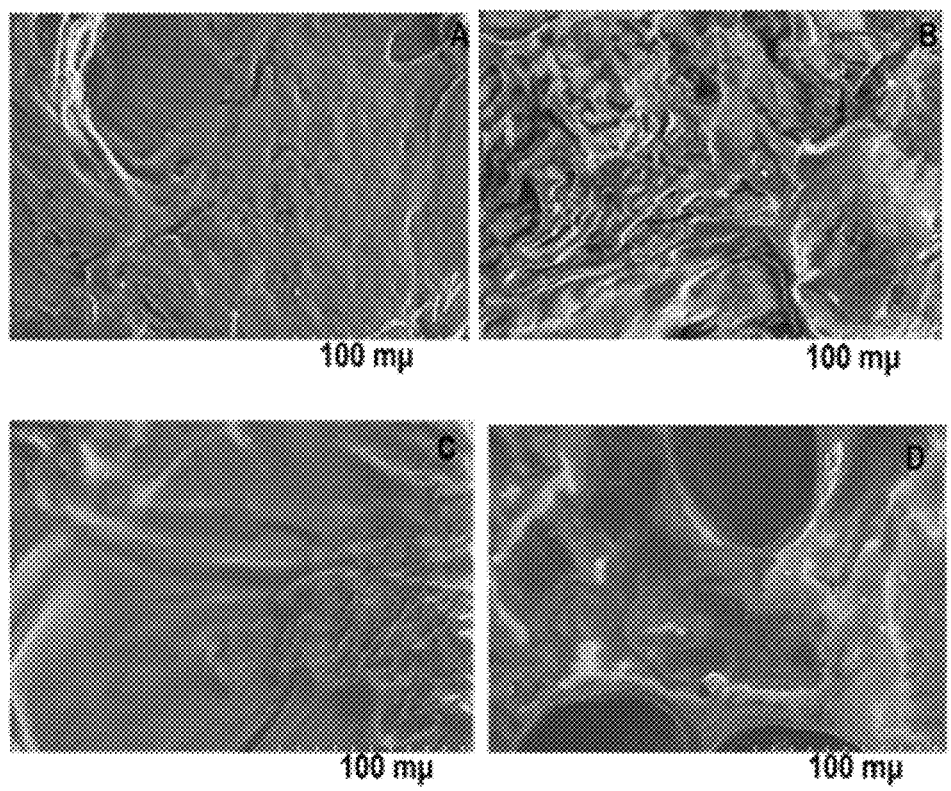
Figure 6A:
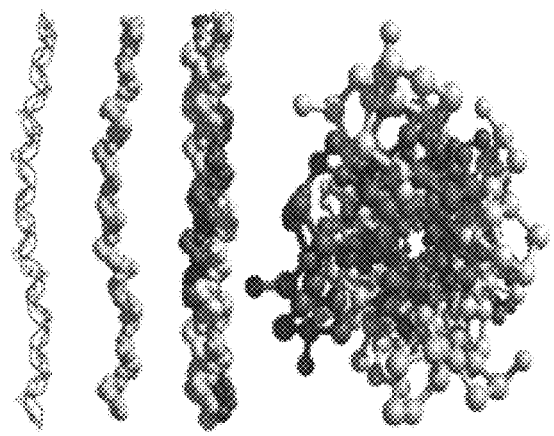
FIG. 6A shows an example of the structure of collagen and how gelatin re-aligns to form its own structure while forming a jelly, the stabilization pathway of the collagen chains is by means of steric repulsion of the pyrrolidine rings pertaining to the hydroxyproline residues.
Figure 6B:
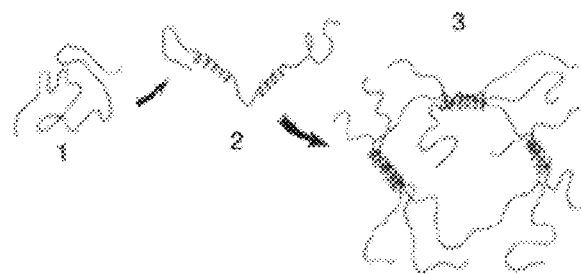
FIG. 6B shows the normal rearrangement of the gelatin and the shape of the collagen structure; when the composition of the present invention is added, it is probable that bonds are formed between other amino acid residues that can replace or complement the hydroxyproline residues. Table 7 shows the residues present in gelatin, and points out those that could form new bonds.

Table 7 shows the results of the residues which, when the synergistic composition of the present invention is added to the gelatin, can form bonds to rearrange the gelatin into the structures shown in FIG. 5.

How do proteins modify themselves to form trabeculae and how do they regain their lost activity? The following data, which have been obtained with other elastic proteins or enzymes, both in our work group and in the literature, are presented.

It was believed that the bonding between elastic proteins, especially flour elastic proteins, was caused by disulfide bonds between cysteine residues; however, in works such as those of Gerrard et al. ("Effects of microbial transglunaminase on the wheat proteins of bread and croissant dough." Journal of Food Science. 2001; 66:782-78) and Tilley et al. ("Tyrosine cross-links: molecular basis of gluten structure and function." Journal of Agricultural and Food Chemistry. 2001), where they identify bonds between lysines, glutamine and tyrosines, the presence of bonds between amino acids other than cysteines is not a new finding, an example is abductin and resilin, elastic proteins similar to glutenins (Tatham, A. S. y Shewry, P. R. "Comparative structures and properties of elastic proteins." Philosophical Transactions of the Royal Society B: Biological Sciences. 2002; 357:229-234).

The first protein where the bonds between tyrosine residues were detected was resilin, an elastic protein similar to elastin. Likewise, TDs have been found in animal structural proteins: elastin, fibrin, cuticlin and collagen (Rodríguez-Mateos, A., Millar, S. J., Bhandari, D. G. y Frazier, R. A. "Formation of dityrosine cross-links during breadmaking." Journal of Agricultural and Food Chemistry. 2006; 54:2761-2766). On the other hand, isodithyrosine has been found in plants in extensin as part of the cell wall (Epstein, L. y Lapmort, D. T. A. "An intramolecular linkage involving isodityrosine in extensine." Phytochemistry. 1984; 23:1241-1246, Rodríguez-Mateos, A., Millar, S. J., Bhandari, D. G. y Frazier, R. A. "Formation of dityrosine cross-links during breadmaking." Journal of Agricultural and Food Chemistry. 2006; 54:2761-2766).

As shown in Table 8, elastic proteins are present in all living organisms and have important activity functions.

If we analyze the sequences of collagen and elastin, which are the main proteins that constitute the alveoli of the lungs, and that are responsible for maintaining their tightness and providing elasticity to them, they have the ability to form several bonds; these can be caused by changes in the microenvironment, as well as the formation of these bonds are affected by proteases actions, such as those generated in neutrophilia caused by Covid-19 which produces elastase; there is evidence that bond formation decreases when the extract is exposed to proteases (Tilley, K. A., Benjamin, R. E., Bagorogoza, K. E., Okot-Kotber, B. M., Pakash, O. y Kwen, H. "Tyrosine cross-links: molecular basis of gluten structure and function." Journal of Agricultural and Food Chemistry. 2001; 49:2627-2632). Likewise, these residues can be critical for proteins to oxidize and expose other amino acids that can form bonds.

TABLE 8

Mechanical properties of elastic proteins.

| Protein | Producing organism | Mechanical properties | Reference |
|---|---|---|---|
| Elastin | Animals | Extracellular matrix protein Several functions, both static (e.g. resistance in dermis) and dynamic (e.g. in arteries and lungs, especially alveoli, stores and releases energy quickly). | Keeley et al., 2002; Tatham and Shewry, 2000; Tatham and Shewry, 2002; Urry et al., 2002. |
| Colagen | Animals | Collagen is the most abundant protein in connective tissue and provides different tissues with very characteristic features, ranging from translucency to high tensile strength, as well as energy storage and heat dispersion. | Nimni and Harkness 1988 |
| Extensin | Plants | Responsible for cell wall assembly and cell growth. | Fry, 1982. |
| Resilin | Insects | It provides elasticity to tissues, serves as an energy store and as a shock absorber for vibrations in flight systems. | Haas et al., 2000; Tatham and Shewry, 2002. |
| Abductin | Bivalve mollusks | Functions as a hinge of the inner ligament of the shell. | Denny and Miller, 2006; Tatham and Shewry, 2000. |
| Byssus | Bivalve mollusks | Allows bonding to hard surfaces without breaking due to tidal action. | Sagert and Waite, 2009; Tatham and Shewry, 2000. |
| Flagelliform silk | Spiders | Forms the spiral of the spider's web. | Knight and Vollrath, 2002. |
| Dragaline silk | Spiders | Forms the fall line and the frames of the web. | Knight and Vollrath, 2002. |
| Titin or connectin | Vertebrates | Responsible for the elasticity of striated muscle and responsible for muscle assembly. | Murayama, 1997; Tatham and Shewry, 2000; Tatham and Shewry, 2002. |
| Glutenins | Wheat endosperm | Carbon and nitrogen reserve for embryo development. | Tatham and Shewry, 2000. |

To understand how proteins are modified it is important to compare the amino acid sequences of proteins; that allow us to better understand how proteins are able to form bonds and how these bonds can occur given the amount and proximity that exists between them, as well as other types of bonds with the surrounding environment.

In the amino acid sequences for resilin, extensin, abductin, elastin, glutenide that were searched in the National Center for Biotechnology Information databases, the amino acids with the highest probability of forming bonds are Q: glutamine, Y: tyrosine, C: cysteine and L: lysine.

Lysine residues are present in a variety of proteins and are one of the most reactive residues (Dalle-Donne, I., Rossi, R., Giustarini, D., Gagliano, N. Lusini, L., Milzani, A., Di Simplicio, P. y Colombo, R. "Actin carbonilation: from a simple marker of protein oxidation to revelant signs of several functional impairment." Free Radical Biology & Medicine. 2001b; 31:1075-1083). The presence of bonds between lysine residues in elastic proteins is known in cases such as elastin, collagen and abductin. Elastin and collagen are among the most widely distributed elastic proteins in the animal kingdom, their structure is comprised of a repetitive domain and a non-repetitive domain rich in alanines where lysine-lysine bonds are formed. Abductin is located in the internal hinge ligament of bivalve mollusks and has two lysine and one tyrosine residues in its repetitive domain, which have been proposed as bonding sites (Tatham, A. S. y Shewry, P. R. "Comparative structures and properties of elastic proteins." Philosophical Transactions of the Royal Society B: Biological Sciences. 2002; 357:229-234).

The environment in which proteins are found influences their structure, as well as the formation of bonds that affect them. An example of the above is the work of Dalle-Donne et al. ("Fluorometric detection of dityrosine coupled with HPLC separation for determining actin oxidation." Scientific Communications American Biotechnology Laboratory. 2001a; 34-36), in which they brought actin into contact with oxidizing agents such as HOCI, which causes a change in the structure of the protein, causing the exposure of tyrosines and allowing the formation of dityrosine-type bonds, such exposure increases as the environment becomes more oxidizing.

The work of Welch et al. ("The role of cysteine residues in the oxidation of ferritin." Free Radical Biology and Medicine. 2002; 33:399-408) uses ferritin, which was considered to have activity due to stabilization by disulfide bridge bonds. However, the authors conclude that the cysteines present in this enzyme are not for disulfide formation, but for the protein to be oxidized or reduced at these residues. Consequently, ferritin changes its conformation and causes the formation of mainly dityrosine-like bonds, which are responsible for the stabilization and activity of this protein.

In the case of actin, which lacks of cysteines and is part of the cytoskeleton, studies such as that of Dalle-Donne et al. ("Fluorometric detection of dityrosine coupled with HPLC separation for determining actin oxidation." Scientific Communications American Biotechnology Laboratory. 2001a; 34-36) have been conducted, concluding that the contact of actin with oxidizing agents such as HOCI causes the exposure of tyrosines, allowing the formation of dithyrosine-like bonds, such exposure increases as the environment becomes more oxidizing. In the case of wheat glutenins, Morales ("Modificaciones de la estructura y enlaces de la red formada por las subunidades de gluteninas de alto peso molecular" (Tesis de Lic.)., Universidad de Colima. Facultad de Ciencias Biológicas y Agropecuarias. pp. 72) modified the environment of glutenin subunits using different agents such as cystine, potassium bromate and ascorbic acid, noting that depending on the agent applied, the types of bonds are affected, either decreasing or increasing one or another, especially the dityrosine, lysine, glutamine and cysteine bonds, but he also point out that this combination of oxidizing and reducing agents also demonstrates that there are critical residues that are important for the formation of such bonds, but that other residues, depending on the environment, can replace these residues to generate other types of bonds. According to the results obtained by Welch et al. ("The role of cysteine residues in the oxidation of ferritin." Free Radical Biology and Medicine. 2002; 33:399-408), Dalle-Donne et al. ("Fluorometric detection of dityrosine coupled with HPLC separation for determining actin oxidation." Scientific Communications American Biotechnology Laboratory. 2001a; 34-36) and Morales ("Modificaciones de la estructura y enlaces de la red formada por las subunidades de gluteninas de alto peso molecular" (Tesis de Lic.)., Universidad de Colima. Facultad de Ciencias Biológicas y Agropecuarias. pp. 72), the presence of critical residues and a specific microenvironment are necessary for the formation of bonds in proteins.

With all of the above, in conjunction with the results obtained in this example, and the application of the composition of the present invention to different media such as flour and gelatin, we can point out that the result does not contradict the aforementioned, nor what has been stated by other authors, but rather provides a further explanation of the mechanisms of protein interaction, this will allow to improve treatments in case of diseases, or even to obtain better products in the case of different industries, and above all, it allows to understand how a protein binds with another to acquire the different macroscopic characteristics that they possess.

Example 3

Procedure 3
Spirometry and Chest Radiography

In order to evaluate the effectiveness of the composition of the present invention in the recovery of the damage caused by the SARS-COV-2 virus at pulmonary level, the following procedure was performed:

The effects were studied in 7 patients who were Covid-19 positive, being 3 females and 4 males, ranging in age from 29 to 83 years old.

For this procedure, chest x-rays were obtained in the laboratories of the Ministry of Health of the State of Colima, Mexico, and spirometries were performed in the private laboratory Respiralia by an interventional Pulmonologist.

The analysis of the effect of the damage caused by the SARS-COV-2 virus on the lungs and its effect on the functionality and capacity of the lungs in their breathing process was performed by analyzing the effect in the chest x-rays and assessing its effect on functionality through single spirometry.

In the case of some of the subjects examined, a bronchodilator (salbutamol at therapeutic doses) was administered to determine whether the obstruction was physical and not pulmonary damage. The patients who did not use the synergistic composition of the present invention during the symptoms caused by Covid-19 were two males aged 57 and 30; the patients who stopped using the synergistic composition of the present invention the moment they felt well and tested negative for SARS-COV-2 virus were 2 females and 1 male, aged 33 and 71 years and 82 years, respectively; it should be noted that the 71-year-old female, despite the fact that she stopped using the synergistic composition of the present invention on a regular basis, used it when she had any throat discomfort, whether due to allergy, presence of dust particles or any other external physical factor.

The patient who regularly used the synergistic composition of the present invention post-disease was a male aged 47 years.

Subjects who used the synergistic composition of the present invention during the Covid-19 positive diagnosis, apparently did not present any discomfort, performed their activities in a normal fashion, and did not present apparent disturbances in their respiration.

The 57-year-old patient was admitted to a hospital with Covid-19 disease, presenting respiratory deterioration requiring mechanical ventilation with subsequent torpid evolution, shock, acute respiratory stress syndrome and acute renal injury; he was treated with multiorgan management, showing slight improvement and extubation 12 days after admission, with oxygen-mask support during the following days before his discharge, he also began to present delirium and nosocomial pneumonia, adjusting his antimicrobial treatment, with clinical improvement again and oxygen was gradually withdrawn; he was discharged 19 days after admission. During his discharge he presented with a diagnosis of resolved Covid-19 viral pneumonia, resolved acute respiratory distress syndrome, probable pulmonary thrombotic microangiopathy, systemic arterial hypertension and prolonged immobility syndrome; he also presented neurological sequelae characterized by memory complaints, as well as clinical data of post-traumatic stress disorder characterized by auditory hallucinations that were treated with quetiapine 25 mg every 24 hrs, the patient reports persistent chronic pain in the right pelvic limb, alterations in sensitivity, and loss of strength when walking.

On the day of discharge, the subject commenced the use of the synergistic composition of the present invention with which he is still under treatment, moderate cognitive impairment still persists, with limitations in areas, disorientation of people and time, panic attacks in crowded or closed places, as well as disorientation and misplacement outdoors, which forces him to require a companion; he also presents respiratory distress when performing intense physical exertion such as climbing stairs or long walks.

In the previous paragraphs, the 57-year-old patient is described, since he is the one who presented more damage due to Covid-19, but also the one who provides more evidence of the effect of the synergistic composition of the present invention on the sequelae of this disease as well as the effect on the proteins that confer elasticity to the lungs.

Figure 7A:
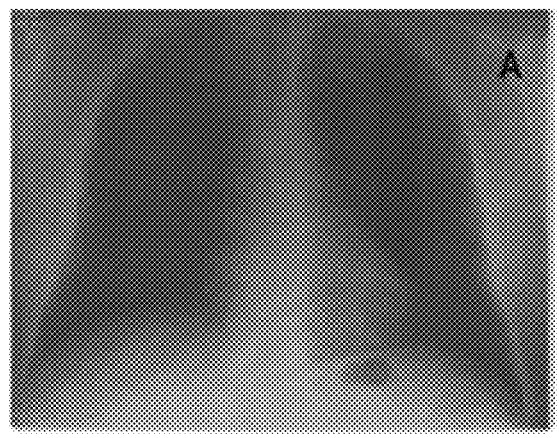

FIG. 7 presents a comparison of the 57-year-old patient's chest x-ray, including a plate before presenting with Covid-19 disease.

As shown in FIG. 7, the 57-year-old patient is free of Covid-19 pneumonia in plate 7A prior to Covid-19 disease, plate 7B was taken after two months after being discharged from hospital with application of the synergistic composition of the present invention, and plate 7C six months after the ingestion of the synergistic composition of the present invention.

Figure 7B:
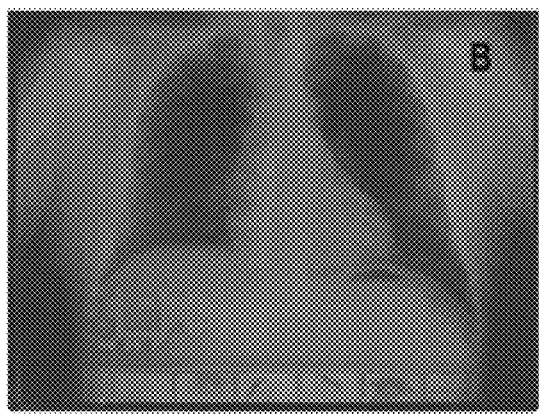
Figure 7C:
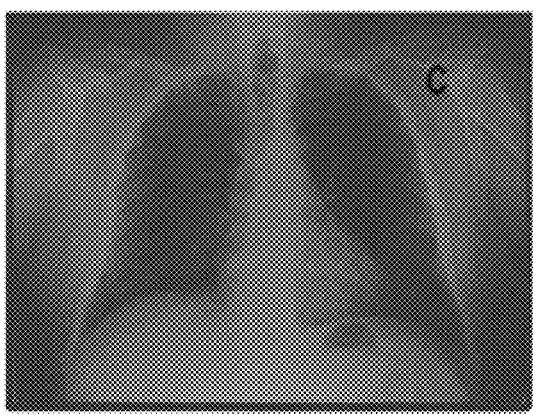

FIG. 7B plate shows that the lung parenchyma presents a larger area of focal opacity with a peripheral and central distribution associated with a diffuse interstitial pattern; the subjective assessment of its extent, both on the plate in FIGS. 7B and 7C, is as follows:

FIG. 7B: Right lung with 25-50% involvement (2 points); left lung with the same involvement as the right lung (2 points); this is based on the modification of the Radiographic Assessment of Lung Edema (RALE)". The total damage in points is 4, according to Table 8.

FIG. 7C: Right lung with <25% involvement (1 point); left lung with the same involvement as the right lung (1 point), based on the RALE classification. The total damage in points is 2 points, according to Table 10.

TABLE 9

Assessment of the extent of the infectious process according to the RALE classification.

| Score | Extension |
| --- | --- |
| 1 | <25% |
| 2 | 25-50% |
| 3 | 50-75% |
| 4 | >75% |

With the damage present in the lungs just 2 months after being hospitalized and requiring assisted ventilation by means of intubation, by taking into account the score in Table 8, and considering Table 9 based on the interpretation of the score in Table 8, it is noted that the condition is mild in plate 7C and moderate in plate 7B.

TABLE 10

Interpretation of damage in the RALE extension

| | |
| --- | --- |
| Mild condition | 1 to 2 points |
| Moderate condition | 3 to 6 points |
| Severe condition | >6 points |

Figure 8:
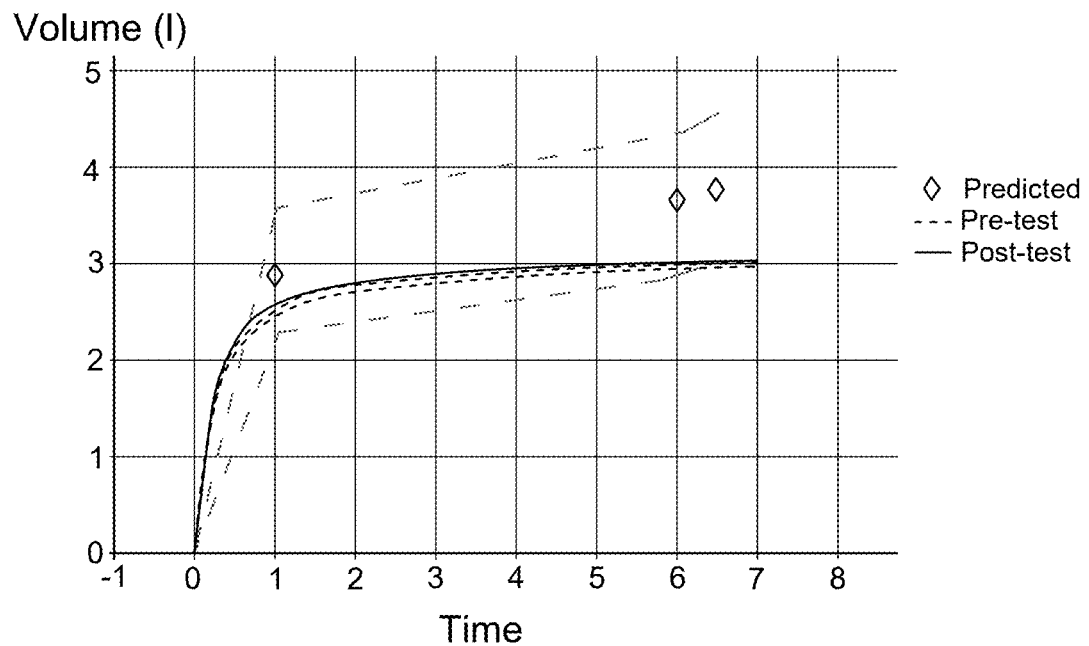

The damage has been in remission with the use of the synergistic composition of the present invention, being more evident and faster at the beginning than 2 months after discharge as can be observed in FIGS. 7B and 7C, demonstrating the progress with a direct pulmonary function study such as a single spirometry 8 months after discharge; as can be observed in FIG. 8, the lungs are at 80% of their capacity according to their maximum forced capacity or FVC (maximum volume of air exhaled), with the maximum possible effort, starting from a maximum inspiration.

Figure 9:
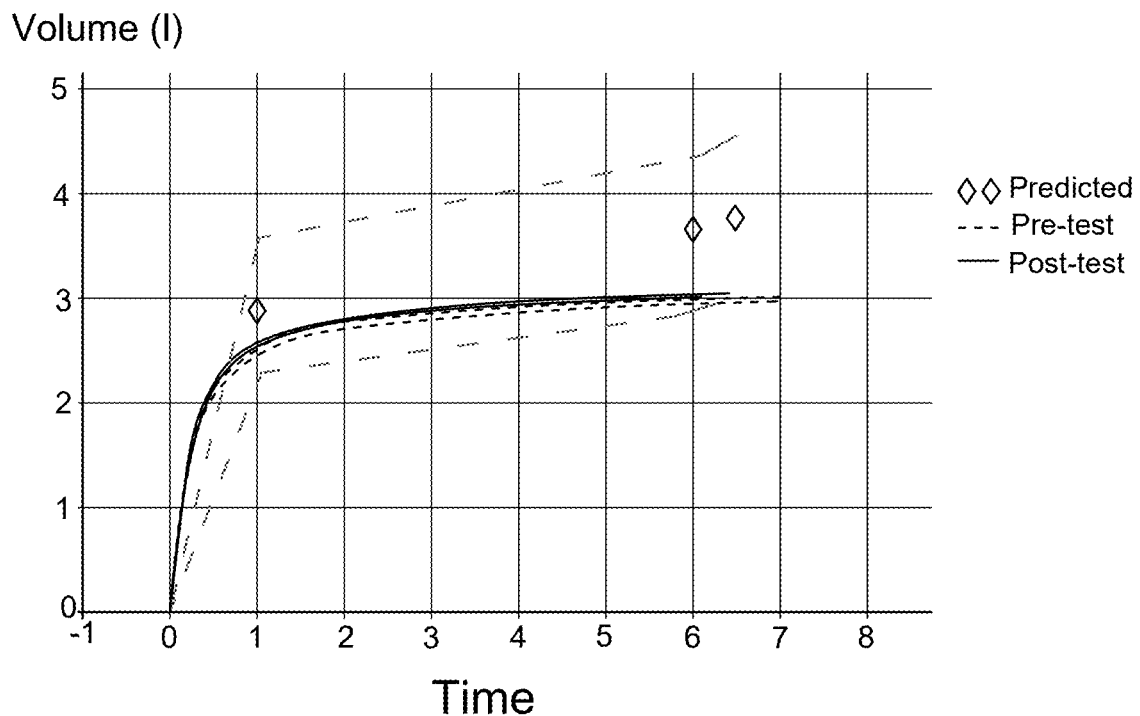

Likewise, there is a mild improvement 4 days after the first test and with the constant use of the synergistic composition of the present invention of 1% (see FIG. 9).

Figure 10:
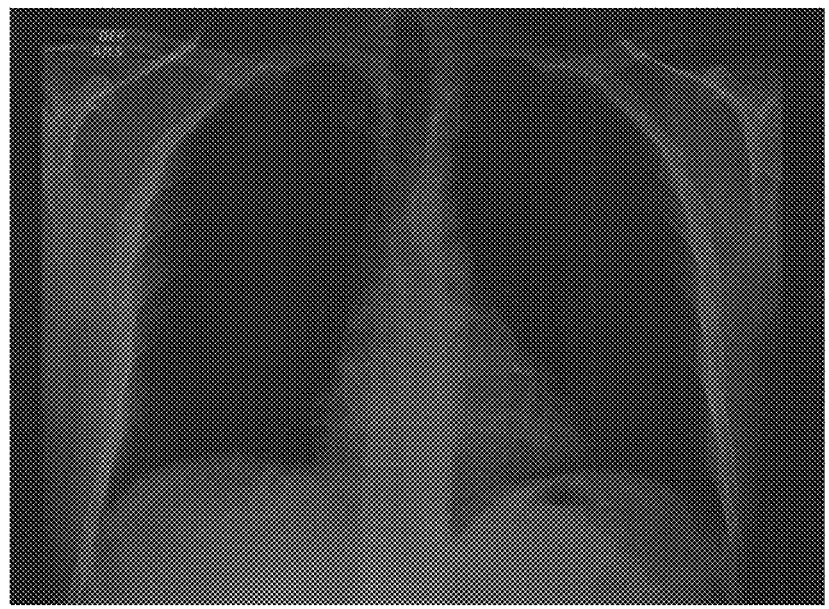

The damage without previous use and during SARS-COV-2 virus infection was severe; however, when initiating the intake of the synergistic composition of the present invention there is a significant improvement, this has allowed the 57-year-old patient to improve, completely eliminating the auditory hallucinations and even climbing stairs, although he still suffers from panic attacks in closed places. When compared to the 30-year-old patient, who also did not use the synergistic composition of the present invention during the SARS-COV-2 virus infection that caused him to develop Covid-19 disease, and who is also the son of the previous patient, this subject did not present any damage at any time in the images taken by chest x-ray (as can be noted in FIG. 10); however, he developed respiratory difficulties with physical exertion.

The 30-year-old patient never presented symptoms of the disease despite testing positive, for this reason he was never in need of any treatment; however, as a result of the positive test, he began to present some physical difficulties, and even developed hypertension, blaming these on other issues unrelated to Covid-19.

Figure 11:
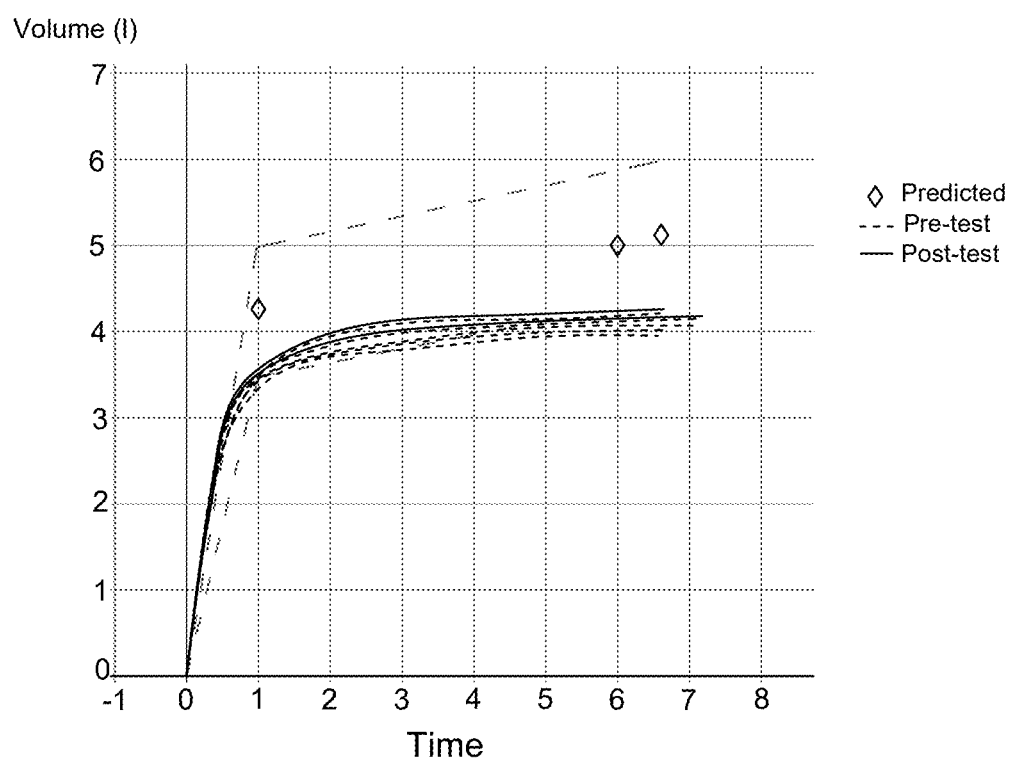

For this reason, since there was no apparent damage, a single spirometry was performed to determine if there was any damage to pulmonary function, especially in gas exchange (see FIG. 11).

As can be observed in FIG. 11, there is moderate damage to lung function, as the maximum volume of air that a subject can exhale in a forced manner from maximum inspiration (FVC) is 87%, indicating that there is a 13% damage in his lungs which prevents him from having a complete exhalation; for this reason he initiated the use of the synergistic composition of the present invention in order to improve his respiratory capacity.

Figure 12:
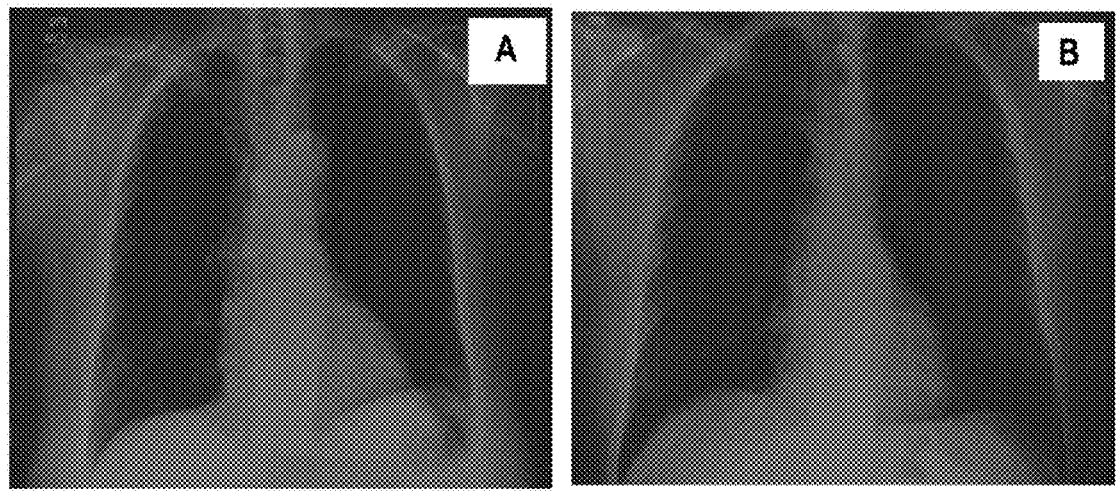

In the following we will describe the subjects who used the synergistic composition of the present invention during the process of SARS-COV-2 infection that resulted in Covid-19 disease; as shown in FIGS. 12A-12B, it is presented the chest x-ray of two subjects where it is shown that both present damage to the lung with different the type of damage; in the case of the 71-year-old woman, the pulmonary parenchyma shows areas of focal opacity with a peripheral and central distribution associated with a diffuse interstitial pattern, the subjective assessment of her extent, according to the RALE in both lungs presents <25% in extent with a score in both lungs of 1 point, is mild according to Table 9 the condition (FIGS. 12A-12B).

The 47-year-old's chest x-ray presents bilateral basal linear images suggesting atelectasis, a lung condition caused by an obstruction of the airways (bronchi or bronchioles) or by pressure on the outside of the lung.

The damage observed in FIGS. 12A-12B of the subjects who used the synergistic composition of the present invention, do not present any symptoms, since both perform their activities in a normal fashion, and even the 47-year-old subject performs high intensity exercise up to 3 hours a day, without presenting any difficulty other than that of the high effort exerted by the exercise he practices (advanced level Crossfit and Boxing). For this reason, both patients underwent single spirometry to determine the effect on lung capacity.

Figure 13:
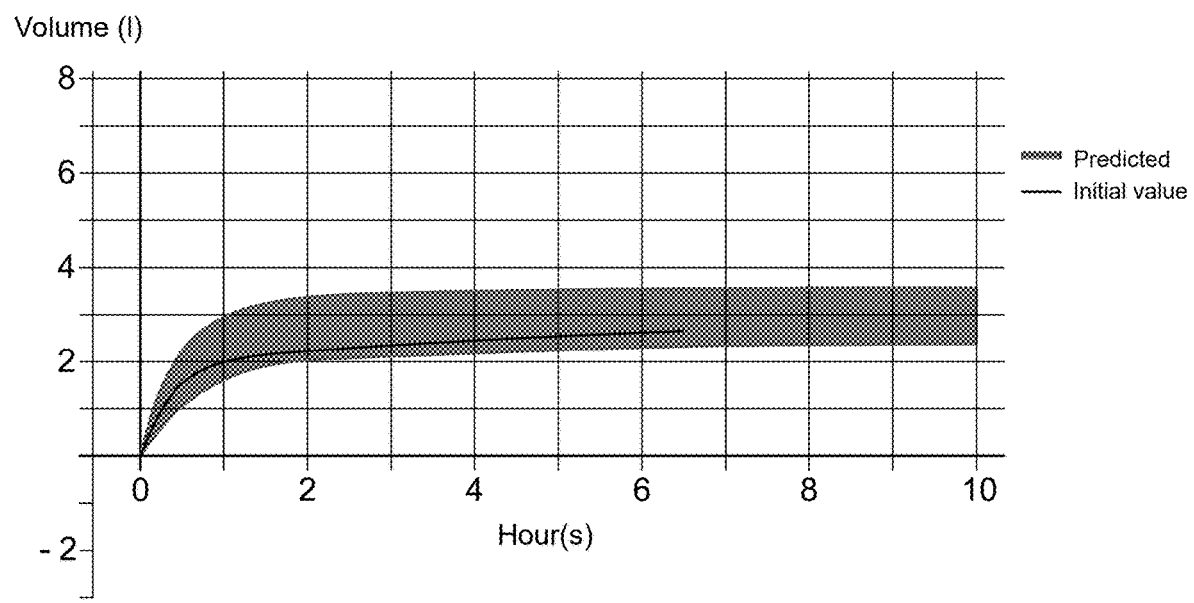

FIG. 13 shows that the 71-year-old female presents a single spirometry that did not require a bronchodilator, since, due to her age, she does not fall within the control parameters, and in spite of that, she has a function above 90%, additionally, for her age she is considered to be in normal condition.

Figure 14:
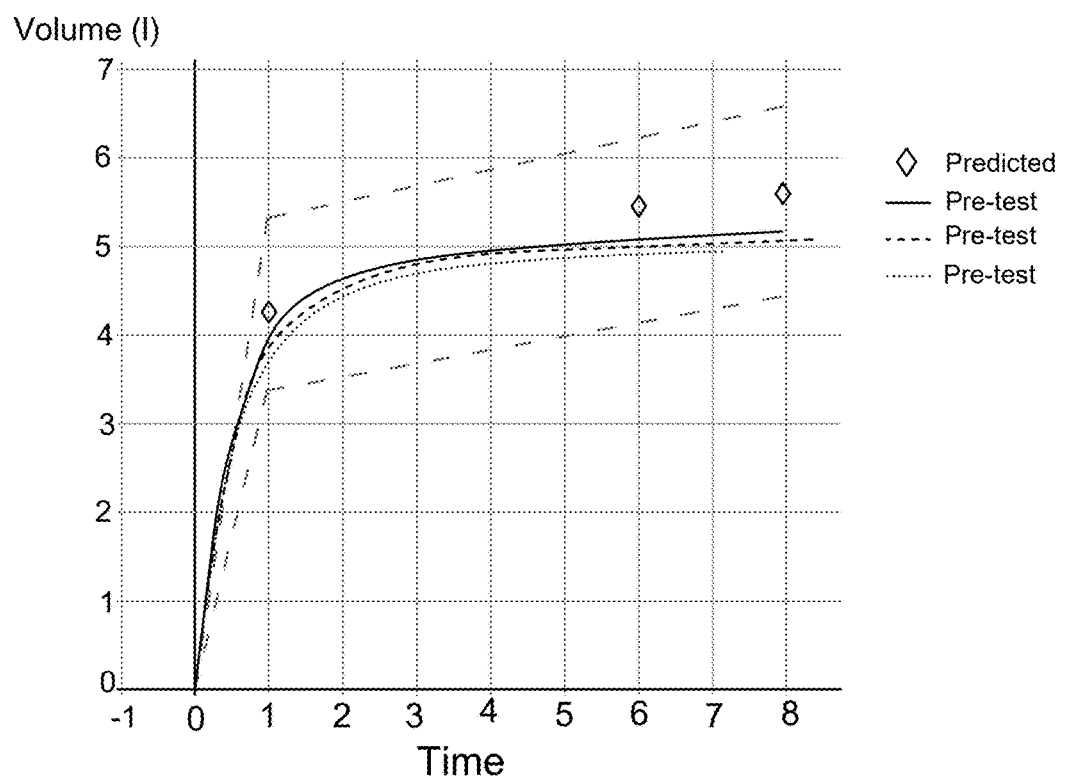

FIG. 14 shows that the single spirometry is in the range of normal spirometry, contrary to the result of the chest x-ray, which according to the interpretation shows atelectasis; therefore, we proceeded to verify it with a ultrasonographic picture, in which we observed a slight lesion of approximately 2% in the left lung and a higher percentage of approximately 5%, similar to that observed for the damage caused by a SARS-COV-2 virus disease, which does not affect the lung's own activity and even in a short time this lesion will disappear.

As shown in FIGS. 13 and 14, there is no visible damage caused by Covid-19 disease in these subjects regarding the proper functionality of the lung, although there is apparent physical damage through chest x-ray or ultrasound, in both cases the damage appears not to affect the functionality of the lungs, and it is probable due to the change that the synergistic composition of the present invention has generated on the lungs similar to what it causes on elastic proteins in the in vitro tests, allowing the new interactions to aid in restoring lung function despite there are areas affected by the action of the SARS-COV-2 virus that causes Covid-19 disease. Not so in patients who did not use the synergistic composition of the present invention, whose functionality is affected even without apparent physical damage as in the 30-year-old patient.

Although the female's age is outside the expected parameters, her lung capacity is so optimal that it even exceeds that of a 65-year-old subject, which according to the physician's subjective interpretation, is considered a normal spirometry.

Figure 15:
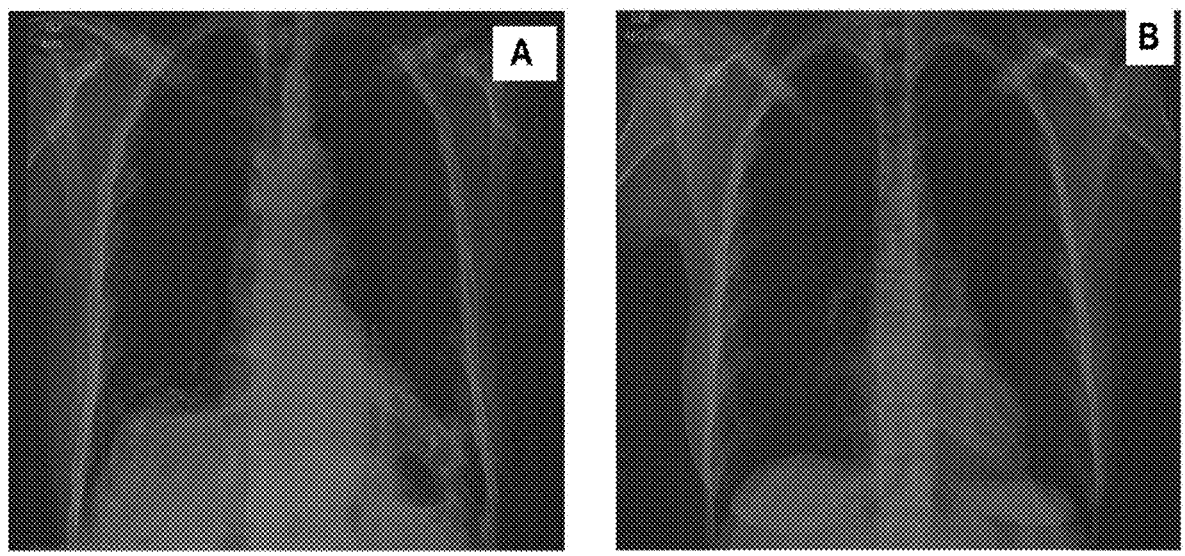

In a particular case, the effect of SARS-COV-2 virus is examined in two patients: an 82-year-old male and a 33-year-old female; in both cases the subjects used the synergistic composition of the present invention during Covid-19 disease, in both cases in the study of the chest x-ray, changes in the lungs were observed, presenting damage in both lungs of the male of <25%, i.e. a slight affectation, and in the case of the female there was only an increase in the bronchovascular tract (see FIG. 15).

FIG. 15 shows that in both cases the data obtained by means of spirometry cannot be validated, that is because there is no validation or predicted value for the 82-year-old male, thus, his data will always be those of a 65-year-old lung, and in the case of the female, because she started a fertilization program and the data would not be valid due to medication and stress; however, both subjects perform their normal activities and even both perform physical activity without pulmonary disturbance.

Figure 16:
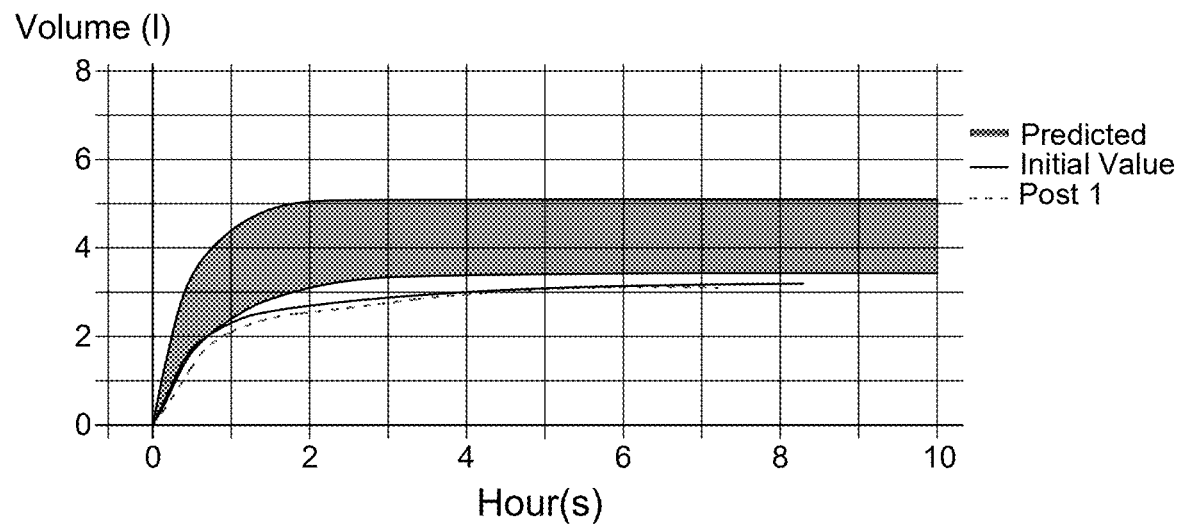

As an example of the above, the spirometry shown in FIG. 16 is useful, there the lung age is 65 years but the FVC1 is 75%, which would indicate a severe impairment of lung function, but given its age, it is considered mild or moderate, hence spirometry is ruled out (FIG. 16).

As shown in FIG. 16, the interpretation will be based on the subjective interpretation of the physician, for that, spirometries of subjects who do not fall within the expected age range or who are undergoing any treatment that may intervene in the pulmonary capacity or response of the subject, are ruled out; yet the 82-year-old subject shows that despite his age, his lungs have a similar functional capacity to a 65 year-old subject, which emphasizes the effect of the synergistic composition of the present invention on the elastic capacity of the proteins of the lungs.

The FVC values for all the subjects are summarized in Table 11, where the value for the 82-year-old subject and the 33-year-old female are discarded given their age and the treatment the female is undergoing.

TABLE 11

Summary of spirometry values for each subject with their percentage of lung capacity.

| | FEV 1 control | FVC control | FEV1 test | FVC test | % Lung capacity |
|---|---|---|---|---|---|
| Male 57 years | 2.92 L | 3.82 L | 2.57 L | 3.05 L | 80 |
| Male 57 years | 2.92 L | 3.82 L | 2.58 L | 3.08 L | 81 |
| Male 30 years | 4.22 L | 5.08 L | 3.59 L | 4.41 L | 87 |
| Male 47 years | 4.42 L | 5.52 L | 4.11 L | 5.12 L | 93 |
| Female 71 years | 2.12 L | 2.77 L | 1.97 L | 2.54 L | 92 |
| Male 82 years | 3.48 L | 4.54 L | 2.44 L | 3.45 L | 76 |
| Female 33 years | 2.91 L | 3.49 L | 2.39 L | 2.83 L | 81 |

*Values discarded because the subjects presented characteristics outside the parameters, the male is 82 years old and the controls are maximum 65 year-old subjects, and the female started a hormone treatment that modifies her general function.

Figure 17:
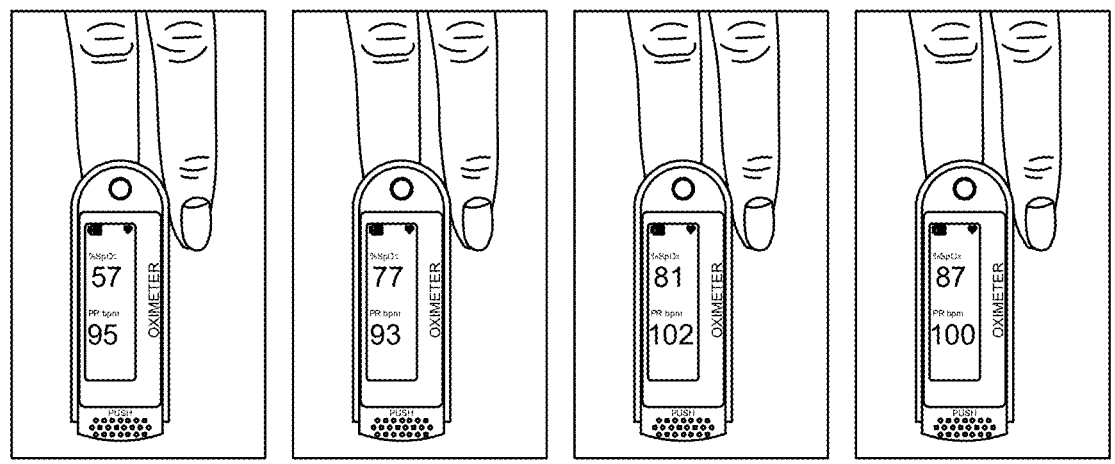

FIG. 17 presents four images of digital pulse oximeters showing the blood oxygen saturation readings of a person who has consumed the synergistic composition of the present invention, exhibiting improvement over time after ingestion of the composition. It can be observed how the synergistic composition of the present invention improves lung capacity immediately during a crisis caused by a disease such as Covid-19; although during the disease, the improvement is not permanent, so the drops of the synergistic composition of the present invention must continue to be applied daily; its use in long-term treatment allows the lungs, even if structural damage is present, to continue or even improve their lung capacity.

The increase in pulse oximeter values occurs with nasal application as well as with sublingual or oral administration, as observed in the images presented in FIG. 17, which were obtained from a subject infected with Covid-19, in these images the synergistic composition of the present invention is administered both nasally and orally at different times.

Example 4

Procedure 4
Pediatric Product

We studied the effect of the synergistic composition to treat respiratory diseases and strengthen the immune system against viral infections such as COVID-19 caused by the SARS-COV-2 virus, other respiratory diseases and other conditions such as infectious and allergic diseases, in the pediatric population; the composition is defined by a mix of a) oil extracted from seeds of the Nigella sativa plant diluted in propyleneglycol with b) alcoholic extract with ethanol from aerial parts of the Asclepias curassavica plant administered in three study groups, the first group consisted of 23 subjects aged 6-24 months, the second group of 34 subjects aged 2-8 years, and the third group of 43 subjects aged 9-15 years; the procedure was as follows:

In a total of 100 subjects, 40 boys and 60 girls with an average age of 5.77 years and ages ranging from 6 months to 15 years, we proceeded as follows:

As described above, in order to prepare the composition of the present invention in its pediatric presentation, the extracts of Nigella sativa and Asclepias curassavica were obtained as previously described, by mixing 500 ml of filtered alcoholic extract of aerial parts of Asclepias curassavica plants and from 300 ml to 500 ml of oil extracted from seeds of Nigella sativa plant in propyleneglycol.

Depending on the discomfort presented by each subject, different combinations of antibiotics, antipyretics and anti-inflammatory drugs were administered.

From the composition of the present invention in its pediatric presentation, 10 drops diluted in 10 ml of water per day, two days a week for 7 weeks were used for the prevention of respiratory diseases or caused by viral infection in subjects aged 9 to 15 years old; for subjects aged 2 to 8 years old the effective dose found was 5 drops diluted in 10 ml of water per day, two days a week for 4 weeks for the prevention of respiratory diseases or diseases caused by viral infection; for subjects aged 6 months to 2 years of age, the dosage was 2 drops diluted in 10 ml of water per day, two days a week for 4 weeks for prevention of respiratory diseases.

Ten drops diluted in 10 ml of water were administered daily, every day in a row to decrease symptoms caused by infection such as SARS-COV-2 virus, influenza virus, asthma, sinusitis and allergies for subjects aged 9 to 15 years during 5 days.

Five drops diluted in 10 ml of water were administered daily, every day in a row to decrease symptoms caused by infection such as SARS-COV-2 virus, influenza virus, asthma, sinusitis and allergies for subjects aged 2 to 8 years during 5 days.

Two drops diluted in 10 ml of water per day, two days a week for 4 weeks were administered for reduction of symptoms caused by throat infection and thrush, for subjects aged 6 months to 24 months. In this group there were no subjects infected by SARS-COV-2 virus, influenza virus, asthma, sinusitis and allergies.

Patients

The study population consisted of 100 subjects who were minors and had the authorization of their parents or legal guardians, who gave their informed consent and acted as responsible for the application of the product with the composition of the present invention in its pediatric presentation. The ages of the minors ranged from 6 months of age to 15-year-old.

Three groups were formed according to the age of the minors, resulting as follows:
Group 1. Minors ranging in age from 6 months to 24 months
Group 2. Minors ranging in age from 2 to 8 years
Group 3. Minors ranging in age from 9 to 15 years Results 4

The groups of children were formed according to their ages once the experiment started, but there was not so much data on children or young people infected with SARS-COV-2 virus, therefore, they were classified by age group, and the number of subjects using the product of the synergistic composition of the present invention in its pediatric presentation was low; however, unfortunately, at present the number of infants, children and young people infected with Covid-19 disease has been increasing.

Table 12 lists the groups and subjects that took part in the analysis of this experiment.

TABLE 12

Groups of infants, children and young people who participated in this work an the diseases they present.

| | No. of subjects | Age | Diseases present (%) |
|---|---|---|---|
| Group 1 | 23 | 6-24 months | 100% throat infection and thrush |
| Group 2 | 34 | 2-8 years | 52% throat infection and thrush<br>22% rhinitis<br>11% recurrent flu<br>15% SARS-COV2 |
| Group 3 | 43 | 9-15 years | 48% throat infection and thrush<br>10% rhinitis<br>9% recurrent flu<br>33% SARS-COV2 |

As shown in Table 11, there are few Covid-19 positive subjects (19 children); but there are already more cases of tests performed on children due to the dramatic increase in infections and death from this pandemic.

With regard to the application of the synergistic composition of the present invention preventively in the case of infants, unfortunately, parents only administer the synergistic composition of the present invention if the infants are infected with Covid-19, even if only mildly, with symptoms of viral infection or any type of respiratory disease.

Therefore, the applications and dosage of the synergistic composition of the present invention were carried out in its pediatric presentation, in a preventive way against Covid-19 when they were negative or it was only a flu, and curative for both respiratory diseases and allergies, and Covid-19; in both cases the doses depended on the group and even the severity of the symptoms of the diseases that each child presented, as summarized in Table 13.

TABLE 13

Dosage and reason for application of the synergistic composition of the present invention for each study group. In the case of groups 2 and 3, preventive are children with symptoms of respiratory diseases or allergies, not Covid-19, and curative is for Covid-19.

| | | % subjects | Dosage of the composition of the invention |
|---|---|---|---|
| Group 1 | Preventive and curative | 100% | 2 times per week during 4 weeks |

TABLE 13-continued

Dosage and reason for application of the synergistic composition of the present invention for each study group. In the case of groups 2 and 3, preventive are children with symptoms of respiratory diseases or allergies, not Covid-19, and curative is for Covid-19.

| | | % subjects | Dosage of the composition of the invention |
|---|---|---|---|
| Group 2 | Preventive | 55% | 2 times per week during 4 weeks |
| | Curative | 45% | 5 days in a row |
| Group 3 | Preventive | 36% | 2 times per week during 7 weeks |
| | Curative | 64% | 5 days in a row |

As in experiment 1, infants, children and young people had reactions to the application of the synergistic composition of the present invention; however, the difference with adults is that for most of the subjects, the reactions were as reported by the parents, and not only that, but most of the reactions reported by the parents were those related to the disease or symptoms that the subjects already had.

The main reaction manifested in infants and children was the presence of nasal flow, which was mild to copious, also in the case that the subject presented any flu-like symptoms.

Another reaction reported in a large percentage was the breathing improvement; this improvement was even observed in the subjects using the synergistic composition of the present invention in the preventive way, similar to that observed in adults, who reported an improvement in their breathing. Table 14, in addition to the reactions, summarizes the observations reported by the parents subsequent to the application of the synergistic composition of the present invention.

TABLE 14

Percentage of subjects presenting reactions and outcomes of the application of composition of the present invention in its pediatric presentation.

| | | | |
|---|---|---|---|
| Decrease in symptoms associated with colds, allergies, and throat infections | 69% | 77% | 64% |

As table 14 shows, nasal discharge is the most common symptom mentioned by parents during the application of the synergic composition of this invention, which is significant because the composition is not applied nasally, or sublingually, but through a 10 ml water solution.

In contrast to the adults, diarrhea was present mainly in infants; moreover, infants under one year of age had diarrhea accompanied by small drops of blood, however, the parents indicated that the diarrhea was painless, and that the individuals did not manifest any discomfort beyond the diarrhea itself, and even this featured few evacuations in a short period of time.

Group 3 revealed no diarrhea reaction, or rather, the children did not point it out.

Parents and children both pointed out that the frequency of their respiratory diseases has decreased, which may be due both to the use of the synergic composition of this invention and to the conditions of social distancing and the use of mouth coverings; however, some parents pointed out that, although in some infants and children the presence of respiratory diseases seemed to remain the same, related symptoms were slighter and less intense than before the application of the synergic composition of the present invention.

Regarding the young people and children who were positive to Covid-19, they manifested both intense headaches and constant vomiting, and that the applications of the synergic composition of this invention caused these symptoms to decrease, and moreover, after the 5 daily applications, the symptoms had subsided entirely.

The application of the synergic composition of this invention, in its version for children, not only caused the individuals' symptoms to subside, but also decreased the manifestation of respiratory and allergic diseases, or at least showed a decrease in the severity of symptoms caused by the respiratory or allergic disease.

Example 5

Procedure 5

A study was conducted on the effect of the synergic composition to treat the side effects of COVID-19 vaccines, as well as on its effect on the antibody production of these vaccines, by employing the synergic composition of this invention as an adjuvant, defined by a mixture of a) oil extracted from seeds of the plant *Nigella sativa* diluted in propylene glycol with b) an alcoholic extract with ethanol obtained from aerial parts of the plant Asclepia curassavica; the study was conducted on a total of 90 individuals, 40 men and 50 women, with an average age of 43.75 and ages ranging from 20 to 82 years old.

The individuals applied one drop per nostril every day for three days in a row, then 1 to 2 applications for a period ranging between 8 and 20 weeks.

The individuals were vaccinated as follows: 50% of them received the Cansino vaccine, 20% Astrazeneca, and 30% the Pfizer vaccine; the Cansino vaccine is a single dose and the other two require two doses.

It is worth noting that some individuals, belonging to both the group that received the synergic composition of this invention and the group that did not, were vaccinated with the same batch, on the same day and at the same place.

Results 5

The side effects manifested by the entirety of the individuals subject to this study are summarized in Table 15, which includes the type of side effect according to vaccine.

TABLE 15

Summary of side effects by vaccine applied.

| | Cansino | Pfizer | Aztraseneca |
|---|---|---|---|
| Fatigue | ✓ | ✓ | ✓ |
| Fever | ✓ | ✓ | ✓ |
| Vomiting | ✓ | | ✓ |
| Arm pain | ✓ | ✓ | ✓ |
| Headaches | | | ✓ |
| Nasal discharge | | ✓ | ✓ |

Table 15 includes the most common symptoms in vaccinated individuals, and does not include isolated occurrences (involving one individual) who presented other symptoms, such as change in taste, general joint pain, shortness of breath, drop in blood pressure, and drowsiness.

All vaccinated individuals who used the mixture of *Asclepias curassavica* and *Nigella sativa* in alcohol and propylene glycol manifested the side effects shown in table 14, but with less intensity. This was measured according to whether they could perform their daily activities; in the case of those vaccinated with Cansino, 100% of them were teachers, both those who used and did not use the synergic composition of this invention. Those who did not use it were not able to work and asked for permission to miss a few days; others, despite teaching online, asked for permission not to log in because they could not even lift the arm where the vaccine was applied.: Individuals who did use the synergistic composition of this invention carried out their activities regularly, and at the end of the day they just . . . felt a little more tired than usual. This group even included individuals who did not manifest any symptoms, all of which reported by the participants.

The same occurred with the other vaccines.

Table 16 shows the percentage of individuals who manifested symptoms and the duration of these symptoms.

TABLE 16

Percentage of individuals who manifested symptoms caused by the vaccines without/with the use of the synergic composition of this invention.

|  | Cansino | | Pfizer | | Aztraseneca | |
| --- | --- | --- | --- | --- | --- | --- |
| Symptoms | Without | With | Without | With | Without | With |
| Fatigue | 85% for one week | 45% for one day | 95% 2 to 5 days | 85% 1 day | 98% 5 to 7 days | 95% 1 to 3 days |
| Fever or low-grade fever | 97% 1 to 5 days | 55% 1 to 3 days | 99% 3 to 7 days | 90% 1 to 3 days | 99% 3 to 7 days | 95% 1 to 3 days |
| vomiting | 50% 1 to 2 days | 25% 1 days | | | 45% 1 to 2 days | 13% 1 to 2 days |
| Arm pain | 55% 1 to 7 days | 35% 1 to 5 days | 99% 1 to 3 days | 99% 1 day | 99% 1 to 3 days | 99% 1 day |
| Headaches | | | | | 80% 1 to 4 days | 20% 1 day |
| Nasal discharge | | | ✓10% 1 to 5 days | 10% 1 day | ✓35% 5 days | 25% 1 day |

As show in table 15, symptoms were similar between those who used and did not use the synergic composition of this invention; the difference was found in the sensation they experienced, as those who used the synergic composition of this invention minimized the severity of the symptoms by pointing out that they were not annoying or disabling; the opposite was true for those who did not use the synergic composition of this invention, as they stated that they felt as if they had been given the disease and that it was very disabling, to the point that they could not perform their daily activities.

The 45 individuals who used the synergic composition of this invention produced antibody test results >250 U/ml, and even individuals who were vaccinated with Astrazeneca or Pfizer vaccines produced 250 U/ml with the first dose.

It is also relevant to point out that individuals who used the synergic composition of this invention and were infected with Covid-19 produced, after 1 month, a higher number of antibodies than those who were infected and did not use the synergic composition of this invention; and based on the 1-month test, individuals who used the synergic composition of this invention produced 250 U/ml of antibodies against Covid-19 after 6 months.

The results are presented with the data provided by external antibody tests conducted by different laboratories.

The following table 17 shows a comparison between two individuals who were vaccinated with the Cansino vaccine, both were infected by Covid-19 in October 2020 and were vaccinated in May 2021, and the antibody test was conducted one month after vaccination.

TABLE 17

Laboratory results showing measurements of Anti SARS-COV-2 antibodies (proteins).

IMMUNOLOGY QUANTITATIVE DETECTION OF ANTI-SARS-COV-2. ANTIBODIES (PROTEIN S)

| COVID 19 ANTI-SARS ANTIBODIES | COV-2 POSITIVE | [REFERENCE VALUE-NEGATIVE] |
| --- | --- | --- |
| QUANTITATIVE VALUE | U/mL | [<0.80 U/mL |

TABLE 17-continued

Laboratory results showing measurements of Anti SARS-COV-2 antibodies (proteins).

| OF 11.30 ANTIBODIES | NEGATIVE] [>0.80 U/mL POSITIVE] |
| --- | --- |

INTERPRETATION
Negative. There is no evidence of previous infection or exposure to SARS-Cov-2. Positive. Probable infection with protective antibodies. The presence of antibodies does not rule out the possibility of reinfection.

IMMUNOLOGY QUANTITATIVE DETECTION OF ANTI-SARS-COV-2. ANTIBODIES (PROTEIN S)

| COVID 19 ANTI-SARS ANTIBODIES | COV-2 POSITIVE | [REFERENCE VALUE-NEGATIVE] [<0.80 U/mL NEGATIVE] |
| --- | --- | --- |
| QUANTITATIVE VALUE OF >250 ANTIBODIES | U/mL | [>0.80 U/mL POSITIVE] |

INTERPRETATION
Negative. There is no evidence of previous infection or exposure to SARS-Cov-2. Positive. Probable infection with protective antibodies. The presence of antibodies does not rule out the possibility of reinfection.

The antibodies generated with the Cansino vaccine, without the benefit of the synergic composition of this invention, produced a value of 11.30 U/mL, compared to 250 U/mL with the use of the synergic composition of this invention.

As shown in Table 17, there is an enormous difference in antibody generation with the use and without the use of the synergic composition of this invention; we acknowledge that individuals who were vaccinated with Cansino, and did not use the synergic composition of this invention, over time are likely to increase the amount of antibodies and achieve adequate protection; however, the use of the synergic composition of this invention is beneficial in terms of immediacy and effectiveness.

Table 18 shows results of individuals after one month of being infected with Covid-19, both of whom used the synergic composition of this invention intensively at the outset of symptoms of the disease.

As shown in table 19, individuals produced antibodies after 6 months at a rate that reached 250U/ml. Individuals who were infected and underwent testing after one month of being infected produced 10 values lower than 8 U/ml, which differs greatly from individuals who used the synergic composition of this invention.

TABLE 18

Antibody results of two individuals with Covid 19 after one month of being infected, both of whom used the synergic composition of this invention intensively at the outset of symptoms of the disease.

Special Test

Detection of high affinity antibodies Cornavirus (Covid-19)

| | | | |
|---|---|---|---|
| High affinity antibodies (INC.IGG) ANTI-SARS-COV-2 | Positive | | [Negative] |
| Quantitative antibody value | 47.68 | COI | Less than 1.0 Negative Greater than 1.0 Positive |

INTERPRETATION:
This test measures high affinity antibodies (including IgG) after 14 days of infection,with a sensitivity greater than 99.5%.
Negative for anti-SARS-Cov-2. There is no evidence of a previous SARS-COV-2 infection (no detection of high affinity antibodies).
Positive for anti-SARS-Cov-2. Probable recent infection with developmental protective antibodies. The presence of antibodies does not rule out the possibility of a new reinfection.
Note: this test is NOT for COVID-19 diagnostic, the WHO recommended method for SARS-Cov-2 is PCR.
Sample: serum.
Method: Electrochemiluminescence.
Team: Cobas e601, ROCHE.

Special Test

Detection of high affinity antibodies Cornavirus (Covid-19)

| | | | |
|---|---|---|---|
| High affinity antibodies (INC.IGG) ANTI-SARS-COV-2 | Positive | | [Negative] |
| Quantitative antibody value | 65.73 | COI | Less than 1.0 Negative Greater than 1.0 Positive |

INTERPRETATION:
This test measures high affinity antibodies (including IgG) after 14 days of infection,with a sensitivity greater than 99.5%.
Negative for anti-SARS-Cov-2. There is no evidence of a previous SARS-Cov-2 infection (no detection of high affinity antibodies).
Positive for anti-SARS-Cov-2. Probable recent infection with developmental protective antibodies. The presence of antibodies does not rule out the possibility of a new reinfection.
Note: this test is NOT for COVID-19 diagnostic, the WHO recommended method for SARS-Cov-2 is PCR.

TABLE 18-continued

Antibody results of two individuals with Covid 19 after one month of being infected, both of whom used the synergic composition of this invention intensively at the outset of symptoms of the disease.

Sample: serum.
Method: Electrochemiluminescence.
Team: Cobas e601, ROCHE.

First antibody reading of 47.68 antibodies in a female individual and a second reading of 65.73 in a male individual after one month of being infected with Covid-19.

TABLE 19

Antibody results of two individuals with Covid-19 after six months of being infected, both of whom used the synergic composition of this invention intensively at the outset of symptoms of the disease.

DESCRIPTION

| | | |
|---|---|---|
| QUANTITATIVE DETECTION OF ANTI-SARS-COV-2 ANTIBODIES (PROTEIN S) | | |
| COVID 19 ANTI-SARS ANTIBODIES | COV-2 POSITIVE | [NEGATIVE] |
| QUANTITATIVE VALUE OF 250.00 ANTIBODIES | U/mL | [<0.80 U/mL NEGATIVE] [>0.80 U/mL POSITIVE] |

INTERPRETATION
Negative. There is no evidence of previous infection or exposure to SARS-COV-2.
Positive. Probable infection with protective antibodies. The presence of antibodies does not rule out the possibility of re infection.
Note: determination of the concentration of neutralized antibodies direct to protein S.
Clinical sensitivity greater than 99.98%.
This test is NOT for diagnostic use of COVID-19, the method recommended by the WHO for SARS-Cov-2 is PCR.
Method: Electrochemiluminescence.

Both individuals, after 6 months of being infected with Covid-19, showed a natural increase in antibodies of 250, and both constantly used the synergic composition of this invention.

The synergic composition of this invention as an adjuvant to the effectiveness of antibody generation should be applied one week before vaccination and two weeks afterwards, as follows: in the morning and the evening, apply one drop in each nostril, and in the afternoon, apply 5 sublingual drops. We can therefore point out that the synergic composition of this invention is a tool that can help mitigate the increase in Covid-19 infections.

The invention has been described sufficiently so that a person with moderate knowledge in the field can reproduce and obtain the results of this invention as mentioned above. However, anyone skilled in the technique related to this invention can make non-descript modifications to this request; however, if these modifications, made in a determined structure or the manufacturing process itself, are relevant to the subject matter of the following claims, such structures must be comprised within the scope of the invention.

We claim:
1. A composition for treating respiratory diseases and strengthening the immune system to combat other diseases, said composition comprising:
 a mixture of a) an oil extracted from seeds of the *Nigella sativa* plant diluted in propylene glycol with b) an alcohol extract with ethanol obtained from aerial parts of the *Asclepias curassavica* plant, wherein hydrogen bonds between the components of the composition are balanced.

2. The composition according to claim 1, wherein the dilution of oil extracted from seeds of the *Nigella sativa* plant in propylene glycol is 2 ml of oil per 1 L of propylene glycol.

3. The composition according to claim 1, wherein said ethanol has a graduation of 96%.

4. The composition according to claim 1, wherein the aerial parts of the *Asclepias curassavica* plant are selected from at least one of stems, green follicles, mature follicles, flowers, dried leaves, fresh leaves, or mixtures thereof.

5. The composition according to claim 1, wherein said mixture comprises a volume of 500 ml to 900 ml of the alcohol extract with ethanol obtained from aerial parts of *Asclepias curassavica* plants; and a volume ranging from 90 ml to 150 ml of the oil extracted from seeds of the *Nigella sativa* plant diluted in propylene glycol.

6. The composition according to claim 1, wherein said mixture comprises a volume of 500 ml of the alcohol extract with ethanol obtained from aerial parts of *Asclepias curassavica* plants; and a volume ranging from 300 ml to 500 ml of the oil extracted from seeds of the *Nigella sativa* plant diluted in propylene glycol.

7. The composition according to claim 1, wherein said composition is administered nasally, orally, sublingually, or anally.

8. The composition according to claim 1, wherein said composition is diluted in water for administration to infants.

9. The composition according to claim 1, wherein said composition is administered at concentrations ranging between 5 µl and 220 µl.

10. The composition according to claim 1, wherein said composition is administered at concentrations ranging between 44 µl and 300 µl.

11. The composition according to claim 1, wherein said composition is administered at a concentration of 10 mg to 50 mg of the extracts.

12. The composition according to claim 1, wherein said composition is used to at least one of treat viral infections and reduce symptoms caused by a SARS-COV-2 virus, protect normal cells from cytopathic effects of the SARS-COV-2 virus, decrease a viral load of the SARS-COV-2 virus in human patients, activate a molecular activity of cellular molecules, reduce side effects produced by an application of vaccines on humans to control the SARS-COV-2 virus, regenerate lung tissue damaged by the SARS-COV-2 virus in humans, increase a function and restructuring of elastic proteins in humans, increase a cardiorespiratory capacity of humans, inhibit damage of cells by disease without affecting normal cells in a patient, regenerate lung tissue damaged by chronic obstructive pulmonary disease (COPD) in humans, reduce symptoms of respiratory diseases, promote modification of a structure of elastic proteins by generating new bonds by modifying a molecular microenvironment of cells and cellular plasticity, or avoid degradation of elastin in the alveoli caused by neutrophilia in infection cases involving the SARS-COV-2 virus.

13. The composition according to claim 1, wherein said composition is administered by drops, capsule, tablet, granules, suppository, gel, or aerosol.

14. A process for preparing a synergic composition for treating respiratory diseases and strengthening the immune system to combat other diseases, said process comprising the steps of:
(a) extracting seed oil from seeds of a *Nigella sativa* plant and diluting said extracted seed oil in propylene glycol;
b) macerating aerial parts of *Asclepias curassavica* plants in ethanol, resting and filtering said macerated aerial parts to obtain a filtered alcohol extract; and
c) mixing said filtered alcohol extract with said extracted oil diluted in propylene glycol.

15. The process according to claim 14, wherein said seed oil is extracted by cold pressing.

16. The process according to claim 14, wherein said seed oil contains from 1 to 2% of Thymoquinone.

17. The process according to claim 14, wherein said diluted extracted seed oil contains between 1 to 4 ml of extracted seed oil per 1 liter of propylene glycol.

18. The process according to claim 14, wherein 20 to 50 g of said aerial parts of *Asclepias curassavica* plants are macerated in 1 liter of ethanol.

19. The process according to claim 14, wherein said macerated aerial parts rest between 12 to 24 hours if subjected to a water bath or between 48 to 72 hours if not subjected to a water bath.

20. The process according to claim 19, wherein said macerated aerial parts are subjected to a water bath for 10 to 15 minutes.

21. The process according to claim 14, wherein a volume of 500 ml to 900 ml of said filtered alcohol extract is mixed with a volume of 100 ml to 500 ml of said extracted oil diluted in propylene glycol.

22. The process according to claim 14, wherein said filtered alcohol extract is obtained by macerating in said ethanol 2 stems of 30 cm of said *Asclepias curassavica* plants, 2 to 4 follicles of said *Asclepias curassavica* plants, and 3 flowers of said *Asclepias curassavica* plants; subjecting said macerated aerial parts to a water bath for 15 minutes; and resting for 12 to 24 hours.

23. The process according to claim 22, wherein the follicles of said *Asclepias curassavica* plants comprise 50% of mature follicles and 50% of green follicles.

24. The process according to claim 14, wherein said filtered alcohol extract is obtained by macerating in said ethanol between 15 and 21 grams of leaves of said aerial parts of *Asclepias curassavica* plants, 4 to 7 grams of follicles of said aerial parts of *Asclepias curassavica* plants, from 5 to 10.2 grams of stems of said aerial parts of *Asclepias curassavica* plants, and 1 gram of flowers of said aerial parts of *Asclepias curassavica* plants.

25. The process according to claim 24, wherein said macerated aerial parts are subjected to a water bath for 10 to 15 minutes and rest between 12 to 24 hours.

26. The process according to claim 24, wherein said macerated aerial parts rest between 48 to 72 hours.

* * * * *